US009132125B2

(12) United States Patent
Mickle et al.

(10) Patent No.: US 9,132,125 B2
(45) Date of Patent: *Sep. 15, 2015

(54) BENZOIC ACID, BENZOIC ACID DERIVATIVES AND HETEROARYL CARBOXYLIC ACID CONJUGATES OF HYDROCODONE, PRODRUGS, METHODS OF MAKING AND USE THEREOF

(71) Applicant: KemPharm, Inc., Coralville, IA (US)

(72) Inventors: Travis Mickle, Celebration, FL (US);
Sven Guenther, Coralville, IA (US);
Christal Mickle, Celebration, FL (US);
Guochen Chi, Coralville, IA (US);
Jaroslaw Kanski, Blacksburg, VA (US);
Andrea K. Martin, Fincastle, VA (US);
Bindu Bera, Blacksburg, VA (US)

(73) Assignee: KemPharm, Inc., Coralville, IA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/557,570

(22) Filed: Dec. 2, 2014

(65) Prior Publication Data
US 2015/0087667 A1 Mar. 26, 2015

Related U.S. Application Data

(63) Continuation of application No. 13/888,587, filed on May 7, 2013, now Pat. No. 8,927,716, which is a continuation of application No. 12/828,381, filed on Jul. 1, 2010, now Pat. No. 8,461,137.

(60) Provisional application No. 61/222,718, filed on Jul. 2, 2009.

(51) Int. Cl.
| A61K 45/06 | (2006.01) |
| A61K 31/485 | (2006.01) |
| A61K 47/48 | (2006.01) |
| C07D 491/08 | (2006.01) |
| C07D 489/04 | (2006.01) |
| A61K 31/167 | (2006.01) |

(52) U.S. Cl.
CPC ............ *A61K 31/485* (2013.01); *A61K 31/167* (2013.01); *A61K 45/06* (2013.01); *A61K 47/48038* (2013.01); *A61K 47/48138* (2013.01); *C07D 489/04* (2013.01); *C07D 491/08* (2013.01)

(58) Field of Classification Search
CPC .. C07D 491/08; C07D 489/04; A61K 31/485; A61K 31/167
USPC .......................... 514/160, 161, 282, 557, 629
See application file for complete search history.

(56) References Cited

U.S. PATENT DOCUMENTS

| 1,731,152 | A | 10/1929 | Schopf |
| 4,668,685 | A | 5/1987 | Shami |
| 7,375,082 | B2 | 5/2008 | Mickle et al. |
| 7,375,083 | B2 | 5/2008 | Mickle et al. |
| 8,461,137 | B2 | 6/2013 | Mickle et al. |
| 8,748,413 | B2 | 6/2014 | Mickle et al. |
| 8,759,368 | B2 | 6/2014 | Mickle et al. |
| 8,828,978 | B2 | 9/2014 | Mickle et al. |
| 8,871,780 | B2 | 10/2014 | Mickle et al. |
| 8,927,716 | B2 | 1/2015 | Mickle et al. |
| 2004/0180036 | A1 | 9/2004 | Ashton |
| 2004/0204434 | A1 | 10/2004 | Shafer |
| 2004/0254182 | A1 | 12/2004 | Mulvihill |
| 2005/0176646 | A1 | 8/2005 | Mickle et al. |
| 2006/0167258 | A1 | 7/2006 | Likhotvorik et al. |
| 2008/0090771 | A1 | 4/2008 | Moncrief |
| 2008/0132570 | A1 | 6/2008 | Xiang |
| 2009/0156820 | A1 | 6/2009 | Wang et al. |
| 2011/0002990 | A1 | 1/2011 | Mickle et al. |
| 2011/0002991 | A1 | 1/2011 | Mickle et al. |
| 2012/0142719 | A1 | 6/2012 | Mickle et al. |
| 2012/0142720 | A1 | 6/2012 | Mickle et al. |
| 2013/0245265 | A1 | 9/2013 | Mickle et al. |
| 2013/0252994 | A1 | 9/2013 | Mickle et al. |
| 2013/0259909 | A1 | 10/2013 | Mickle et al. |
| 2015/0065536 | A1 | 3/2015 | Mickle et al. |

FOREIGN PATENT DOCUMENTS

| AT | 229 496 B | 9/1963 |
| EA | 8864 B1 | 8/2007 |
| GB | 320749 | 10/1920 |
| WO | 92/08459 | 5/1992 |

(Continued)

OTHER PUBLICATIONS

Bertram, F. and W. Stoltenberg, "Kinische Erfahrungen Mit Acedicon," Klinische Wochenschrift, 8, Jahrgang, Nr. 19, 1929, pp. 883-886.
Bradford, L.W. and J.W. Brackett, "Systematic Procedure for the Identification of Dangerous Drugs, Poisons, and Narcotics by Ultraviolet Spectrophotometry," Laboratory of Criminalistics, 1956, pp. 353-382.
Catlin, D.H., "Analytical Chemistry and the Games of the XXIIIrd Olympiad in Los Angelos, 1984," Clin. Chem., 1987, pp. 319-327.
Fischer, R. and M.S. Karawia, "Zum Nachweis von Analgeticis und Alkaloiden Mittels Tetraphenylbornatrium (Kalignost) und Nitrokorpern," Aus dem Pharmakognostischen Institut der Universitat Graz, 1953, pp. 366-374.
Hosztafi, S., Köhegyi, I., Simon, C., Fürst, Z., "Synthesis and Analgetic Activity of Nicotinic Esters of Morphine Derivatives" Arzneimittel-Forschung [1993, 43(11):1200-1203].
Hydrocodone chemical structure (ChemSpider, last visit Sep. 18, 2013).

(Continued)

*Primary Examiner* — Jennifer M Kim
(74) *Attorney, Agent, or Firm* — McAndrews, Held & Malloy, Ltd.

(57) ABSTRACT

The presently described technology provides compositions comprising aryl carboxylic acids chemically conjugated to hydrocodone (morphinan-6-one, 4,5-alpha-epoxy-3-methoxy-17-methyl) to form novel prodrugs/compositions of hydrocodone, including benzoates and heteroaryl carboxylic acids, which have a decreased potential for abuse of hydrocodone. The present technology also provides methods of treating patients, pharmaceutical kits and methods of synthesizing conjugates of the present technology.

30 Claims, 15 Drawing Sheets

(56) References Cited

FOREIGN PATENT DOCUMENTS

| WO | 96/16063 | 5/1996 |
|---|---|---|
| WO | 2005/032474 | 4/2005 |
| WO | 2007/140272 A2 | 12/2007 |
| WO | 2011/008636 A1 | 1/2011 |
| WO | 2011002991 | 6/2011 |
| WO | 2011002995 | 6/2011 |

OTHER PUBLICATIONS

Jane, I., A. McKinnon, and R.J. Flanagan, "High-Performance Liquid Chromatographic Analysis of Basic Drugs on Silica Columns Using Non-Aqueous Ionic Eluents. II. Application of UV, Flourescence and Electrochemical Oxidation detection," Journal of Chromotography, 1985, pp. 191-225.

Leland, D.L., J.O. Polazzi and M.P. Kotick, "Preparation of 7-beta-Methyldihydrothebaine," J. Org . Chem., 1980, pp. 4026-4028.

Micheel, F. and W. Leifels, "Papierchromatographische Trennungen von Alkaloidgemischen an Succinylzellulose-Papieren," Aus dem Organisch-chemischen Institute der Universitate Munster, 1960.

Perrigo et al., "Use of Dual-Column Fused-Silica Capillary Gas Chromatography in Combination with Detector Response Factors for Analytical Toxicology," Journal of Chromatography, 1985 pp. 81-88.

Persson-Stubberud, Karin and Astrom, Ove, "Separation of ibuprofen, codeine phosphate, their degradation products and impurities by capillary electrophoresis I. Method development and optimization with fractional factorial design," J. of Chromatogrphy A, 798 (1998) pp. 307-314.

Small, L., H.M. Fitch and W.E. Smith, "The Addition of Organomagnesium Halides to Pseudocodeine Types. II. Preparation of Nuclear Alkylated Morphine Derivatives," Preparation of Nuclear Alkylated Morphine Derivatives, J. Am. Chem. Soc., 1936, pp. 1457-1463.

Small, L., S. G. Turnbull, and H.M. Fitch, "The Addition of Organomagnesium Halides to Pseudocodiene Types. IV. Nuclear-Substituted Morphine Derivatives," J. Org . Chem., 1938, pp. 204-232.

Thebacon—List of Thebacon suppliers; SciFinder Scholar, Report for CAS RN 466-90-0, 2011.

Von Ernst Vidic, "Eine neue Schnellmethode zur Untersuchung von Urin auf Opiate und deren Derivate," Aus den institut fur gerichtliche und soziale Medizin der Freien Universitat Berlin, 1951.

International Search Report in PCT/US2010/040775, dated Aug. 16, 2010.

International Search Report in PCT/US2010/040785, dated Aug. 20, 2010.

Office Action in U.S. Appl. No. 12/828,381, dated Aug. 1, 2012.
Office Action in U.S. Appl. No. 12/828,456, dated Aug. 21, 2012.
Office Action in U.S. Appl. No. 12/828,381, dated Nov. 8, 2012.
Office Action in U.S. Appl. No. 12/828,456, dated Dec. 19, 2012.
Office Action in U.S. Appl. No. 12/828,456, dated Feb. 6, 2013.
Office Action in U.S. Appl. No. 13/378,857, dated Feb. 22, 2013.
Notice of Allowance in U.S. Appl. No. 12/828,381, dated Mar. 25, 2013.
Office Action in U.S. Appl. No. 13/378,857, dated May 23, 2013.
Office Action in U.S. Appl. No. 13/888,578, dated Jul. 2, 2013.
Notice of Allowance in U.S. Appl. No. 12/828,456, dated Jul. 24, 2013.
Office Action in U.S. Appl. No. 13/888,583, dated Aug. 2, 2013.
Notice of Allowance in U.S. Appl. No. 13/888,578, dated Sep. 4, 2013.
Office Action in U.S. Appl. No. 13/788,800, dated Sep. 19, 2013.
Office Action in U.S. Appl. No. 13/378,857, dated Sep. 25, 2013.
Notice of Allowance in U.S. Appl. No. 13/888,578, dated Feb. 10, 2014.
Notice of Allowance in U.S. Appl. No. 13/378,800, dated Mar. 6, 2014.
Notice of Allowance in U.S. Appl. No. 13/888,583, dated May 2, 2014.
Notice of Allowance in U.S. Appl. No. 12/828,456, dated Jul. 22, 2014.
Notice of Allowance in U.S. Appl. No. 13/888,587, dated Sep. 12, 2014.
Office Action in U.S. Appl. No. 14/493,611, dated Dec. 16, 2014.
Notice of Allowance in U.S. Appl. No. 14/493,611, dated Mar. 24, 2015.
European Patent Office, Communication with Extended European Search Report in application No. 10794752.4, dated May 6, 2015 (12 pages).

FIGURE 4

4A. Common hydrocodone products and dosage ranges

| Second API | | Hydrocodone Bitartrate |
|---|---|---|
| Name | Strength | Strength[a] |
| acetaminophen | 300 mg | 5 mg |
| | | 7.5 mg |
| | | 10 mg |
| | 325 mg | 5 mg |
| | | 7.5 mg |
| | | 10 mg |
| | 400 mg | 5 mg |
| | | 7.5 mg |
| | | 10 mg |
| | 500 mg | 2.5 mg |
| | | 5 mg |
| | | 7.5 mg |
| | | 10 mg |
| | 650 mg | 7.5 mg |
| | | 10 mg |
| | 660 mg | 10 mg |
| | 750 mg | 7.5 mg |
| | | 10 mg |
| ibuprofen | 200 mg | 2.5 mg |
| | | 7.5 mg |
| | | 10 mg |
| aspirin | 500 mg | 2.5 mg |
| | | 5 mg |
| | | 7.5 mg |
| chlorpheniramine maleate | 2 mg | 5 mg |
| | 4 mg | |
| | 8 mg | 10 mg |
| phenylpropanolamine hydrochloride | 12.5 mg | 2.5 mg |
| | 25 mg | 5 mg |
| phenylephrine hydrochloride | 5 mg | 1.66 mg |
| | 10 mg | 3.75 mg |
| pseudoephedrine hydrochloride | 60 mg | 5 mg |
| phenylephrine hydrochloride | 5 mg | 1.66 mg |
| | | 3.75 mg |
| guaifenesin | 100 mg | 5 mg |
| | 300 mg | |

FIGURE 4 (continued)

4B. Common hydrocodone products and dosage ranges (continued)

| Hydrocodone Bitartrate | Second API | | Third API | |
|---|---|---|---|---|
| Strength[a] | Name | Strength | Name | Strength |
| 5 mg | homatropine methylbromide | 1.5 mg | na | |
| 2.5-10 mg | acetaminophen | 300-750 mg | na | |
| 2.5-10 mg | ibuprofen | 200 mg | na | |
| 5-10 mg | chlorpheniramine maleate | 4-8 mg | na | |
| 2.5-7.5 mg | aspirin | 500 mg | na | |
| 2.5-5 mg | phenylpropanolamine hydrochloride | 12.5-25 mg | na | |
| 1.66-3.75 mg | phenylephrine hydrochloride | 5-10 mg | na | |
| 5 mg | pseudoephedrine hydrochloride | 60 mg | na | |
| 5 mg | guaifenesin | 100-300 mg | na | |
| 1.66-3.75 mg | phenylephrine hydrochloride | 5 mg | pyrilamine maleate | 8.33 mg |
| 5 mg | chlorpheniramine maleate | 2 mg | pseudoephedrine hydrochloride | 30 mg |

[a]Doses of hydrocodone prodrugs of this invention can be calculated from hydrocodone bitartrate (conversion formula was listed in previous invention disclosure document).

Oral PK Profiles (HC)
Bz-HC vs. YYFFI-HC vs. Diglycolate-HC

Oral PK Profiles (HM)
Bz-HC vs. YYFFI-HC vs. Diglycolate-HC

Intranasal PK Profiles (HC)
Bz-HC vs. Adipate-HC

Intranasal PK Profiles (HM)
Bz-HC vs. Adipate-HC

Oral PK Profiles (HC)
Bz-HC vs. Nicotinate-HC vs. Hydrocodone·BT

Oral PK Profiles (HM)
Bz-HC vs. Nicotinate-HC vs. Hydrocodone·BT

Oral PK Profiles (HC)
Bz-HC vs. 2-ABz-HC vs. Hydrocodone·BT

Oral PK Profiles (HM)
Bz-HC vs. 2-ABz-HC vs. Hydrocodone·BT

FIGURE 13
13A. Synthesis of Benzoate-Hydrocodone
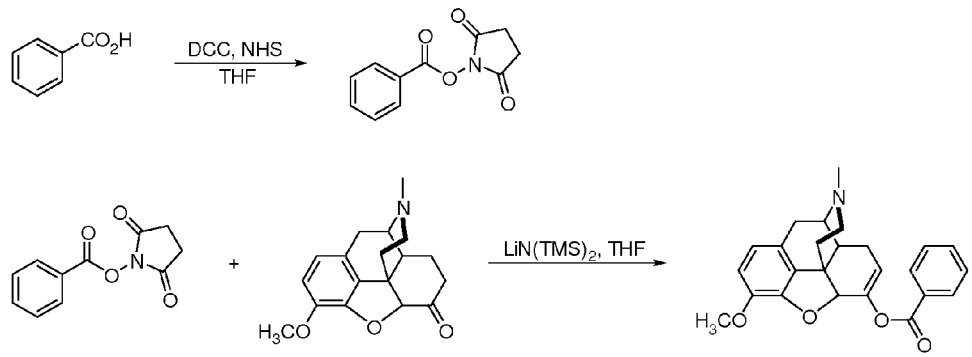
13B. Synthesis of Nicotinate-Hydrocodone
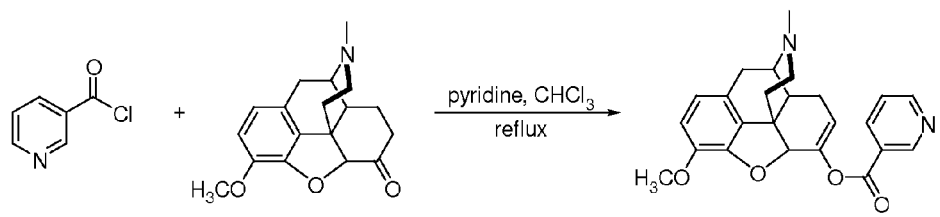

FIGURE 13 (Continued)
13C. Synthesis of 2-Aminobenzoate-Hydrocodone
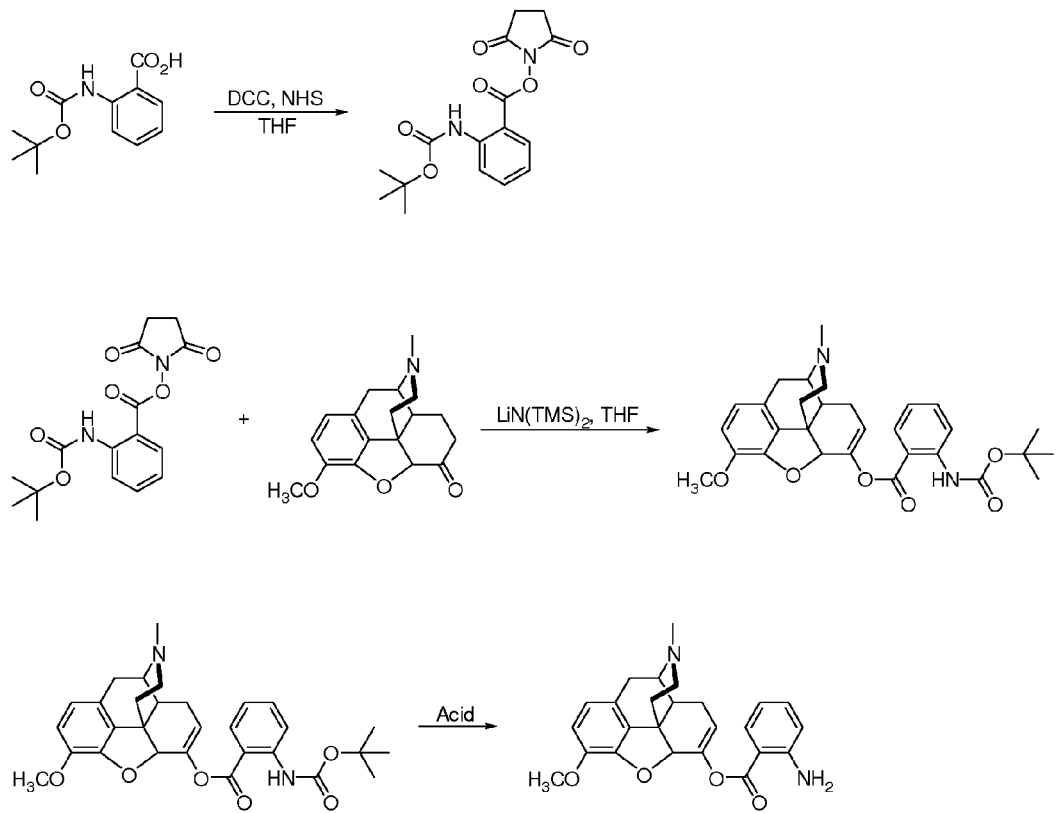
13D. Synthesis of Salicylate-Hydrocodone
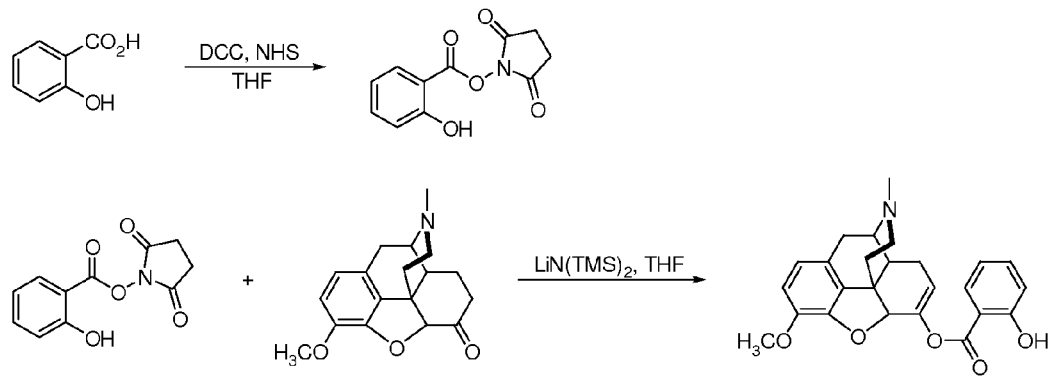

Oral PK Profiles
Bz-HC (HC, HM, intact prodrug)

Oral PK Profiles (HC) in Dogs
Bz-HC vs. Hydrocodone·BT

Oral PK Profiles (HM) in Dogs
Bz-HC vs. Hydrocodone·BT

Oral PK Profiles in Dogs
Bz-HC (HC, intact prodrug)

Intravenous PK Profiles
Bz-HC (HC, HM, intact prodrug)

Oral Dose Range Study (HC)
Bz-HC

Oral Dose Range Study (HM)
Bz-HC

BENZOIC ACID, BENZOIC ACID DERIVATIVES AND HETEROARYL CARBOXYLIC ACID CONJUGATES OF HYDROCODONE, PRODRUGS, METHODS OF MAKING AND USE THEREOF

RELATED APPLICATIONS

This application is a continuation of U.S. application Ser. No. 13/888,587, filed May 7, 2013, which is a continuation of U.S. application Ser. No. 12/828,381, filed Jul. 1, 2010, now U.S. Pat. No. 8,461,137, which claims priority to and benefit of U.S. provisional patent application No. 61/222,718, filed Jul. 2, 2009, both of which are herein incorporated by reference in their entireties.

FEDERALLY SPONSORED RESEARCH OR DEVELOPMENT

[Not Applicable]

BACKGROUND OF THE INVENTION

Opioids are highly effective as analgesics and are commonly prescribed for the treatment of acute and chronic pain. They are also commonly used as antitussives. The opioids, however, also produce euphoria and are highly addictive. As a result they are often abused with far reaching social and health related consequences.

Because of the inherent potential for abuse, it is desirable that any pharmaceutical composition containing an opioid agonist be made as abuse-resistant or abuse-deterrent as practical. Illicit users often will attempt to circumvent the extended release properties of these dosage forms by injecting or otherwise misusing the product in order to achieve an immediate release of the opioid agonist.

Despite their addictive properties and the potential for abuse, morphine-like drugs, particularly, codeine, hydrocodone, and oxycodone have been routinely prescribed as treatment for severe acute and chronic pain in recent decades. This is, in part, because there are no alternatives to relieve severe pain that is resistant to other less potent analgesics such as non-steroidal anti-inflammatory drugs (NSAIDS). In this regard, there is a need to decrease the abuse potential. Thus far, approaches taken, unfortunately, have not solved the problem.

Hydrocodone is an opioid analgesic and antitussive and occurs as fine, white crystals or as crystalline powder. Hydrocodone is a semisynthetic narcotic analgesic prepared from codeine with multiple actions qualitatively similar to those of codeine. It is mainly used for relief of moderate to moderately severe pain. Additionally, it is used as an antitussive in cough syrups and tablets in sub-analgesic doses (2.5-5 mg).

Patients taking opioid analgesics such as hydrocodone for pain relief can become unintentionally addicted. As tolerance to the opioids develops more drug is needed to alleviate the pain and generate the sense of well being initially achieved with the prescribed dose. This leads to dose escalation, which if left unchecked can lead rapidly to addiction. In some cases patients have become very addicted in as little as thirty days.

BRIEF SUMMARY OF THE INVENTION

The present technology utilizes covalent conjugation of the opioid hydrocodone with certain aryl carboxylic acids to decrease its potential for causing overdose or abuse by requiring the active hydrocodone to be released through enzymatic or metabolic breakdown of the conjugate in vivo. The present technology also provides methods of delivering hydrocodone as conjugates that release the hydrocodone following oral administration while being resistant to abuse by circuitous routes such as intravenous ("shooting") injection and intranasal administration ("snorting").

The presently described technology in at least one aspect provides a slow/sustained/controlled release composition of conjugated hydrocodone that allows slow/sustained/controlled delivery of the hydrocodone and/or its active metabolite, hydromorphone, into the blood system of a human or animal within a safe therapeutic window upon, for example, oral administration. At least some compositions/formulations of the current technology can lessen addiction/abuse potential and/or other common side effects associated with hydrocodone and similar compounds.

In one aspect, the present technology provides a composition comprising at least one conjugate of hydrocodone and at least one benzoic acid or derivative thereof, a salt thereof, or a combination thereof, the benzoic acid or derivative thereof having the following formula I:

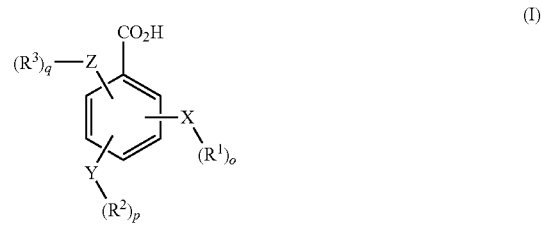

where X, Y and Z are independently selected from the group consisting of H, O, S, NH and $-(CH_2)_x-$; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer between 1 and 10. In some aspects, the benzoic acid or derivative thereof is an aminobenzoate, a hydroxybenzoate, an aminohydroxybenzoate, a derivative thereof, or combination thereof.

In another aspect, the present technology provides a composition comprising at least one conjugate of hydrocodone and at least one benzoic acid, a derivative thereof, or a combination thereof.

In yet another aspect, the present technology provides conjugates of hydrocodone for use to treat pain, preferably moderate to severe pain, or for use to reduce or prevent oral, intranasal or intravenous drug abuse. In some aspects, the conjugates provide oral, intranasal or parenteral drug abuse resistance.

In another aspect, the present technology provides at least one conjugate of hydrocodone that exhibits a slower rate of release over time and a greater or equal AUC when compared to an equivalent molar amount of unconjugated hydrocodone over the same time period. In other aspects, the conjugate of hydrocodone exhibits less variability in the oral PK profile when compared to unconjugated hydrocodone. In yet another aspect, at least one conjugate has reduced side effects when compared with unconjugated hydrocodone or prevents drug tampering by either physical or chemical manipulation.

In another aspect, at least one conjugate is provided in an amount sufficient to provide a therapeutically bioequivalent AUC when compared to an equivalent molar amount of unconjugated hydrocodone. In further aspects, at least one conjugate is provided in an amount sufficient to provide a therapeutically bioequivalent AUC when compared to an equivalent molar amount of unconjugated hydrocodone but does not provide a $C_{max}$ spike or has a lower $C_{max}$ than a therapeutically equivalent amount of unconjugated hydrocodone. In yet a further aspect, at least one conjugate is provided in an amount sufficient to provide a therapeutically bioequivalent AUC when compared to an equivalent molar amount of unconjugated hydrocodone, but does not provide an equivalent $C_{max}$ spike. In some aspects, at least one conjugate provides an equivalent $C_{max}$ spike when compared to unconjugated hydrocodone.

In yet another aspect, the present technology provides a method for treating a patient having a disease, disorder or condition requiring or mediated by binding of an opioid to the opioid receptors of the patient, comprising orally administering to the patient a pharmaceutically effective amount of at least one conjugate of hydrocodone and at least one benzoic acid or derivative thereof, a salt thereof, or a combination thereof, the benzoic acid or derivative thereof having formula I:

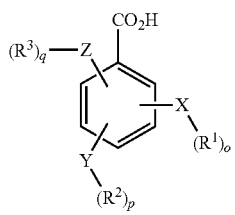

where X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer between 1 and 10.

In another aspect, at least one conjugate binds irreversibly to the opioid receptors of the patient. In yet another aspect, at least one conjugate binds irreversibly to the opioid receptors of the patient without a CNS depressive effect.

In a further aspect, the present technology provides a method for treating a patient having a disease, disorder or condition requiring or mediated by inhibiting binding of an opioid to the opioid receptors of the patient, comprising orally administering to the patient a pharmaceutically effective amount of at least one conjugate of hydrocodone and at least one benzoic acid or derivative thereof, a salt thereof, or a combination thereof, the benzoic acid or derivative thereof having formula I:

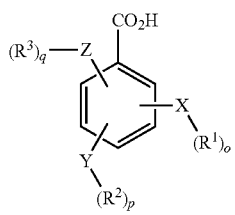

wherein X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer between 1 and 10.

In some aspects, the present technology provides at least one conjugate that reversibly inhibits binding of an opioid to the opioid receptor of the patient. In other aspects, at least one conjugate reversibly inhibits binding of an opioid to the opioid receptor of the patient without a CNS depressive effect.

In a further aspect, the present technology provides a method for treating a patient having a disease, disorder or condition (such as pain) which can be treated by binding of an opioid to the opioid receptors of the patient, the method comprising orally administering to the patient a pharmaceutically effective amount of at least one conjugate of hydrocodone and at least one benzoic acid, a salt thereof, a derivative thereof or a combination thereof.

In another aspect, the present technology provides a method for treating a patient having a disease, disorder or condition (such as addiction) which can be treated by inhibiting binding of an opioid to the opioid receptors of the patient, comprising orally administering to the patient a pharmaceutically effective amount of at least one conjugate of hydrocodone and at least one benzoic acid, a salt thereof, a derivative thereof or a combination thereof.

In yet another aspect, the present technology provides a pharmaceutical kit including a specified amount of individual doses in a package containing a pharmaceutically effective amount of at least one conjugate of hydrocodone and at least one benzoate, a salt thereof, a derivative thereof or a combination thereof, the benzoate having the formula I:

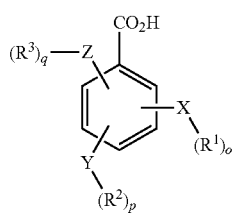

wherein X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q can be independently selected from 0 or 1; and x is an integer between 1 and 10. In some aspects, the kit further comprises instructions for use of the kit in a method for treating or preventing drug withdrawal symptoms or pain in a human or animal patient.

In another aspect, the present technology provides a pharmaceutical kit including a specified amount of individual doses in a package containing a pharmaceutically effective amount of at least one conjugate of hydrocodone and at least one benzoic acid, a salt thereof, a derivative thereof or a combination thereof. In some aspects, the kit further includes instructions for use of the kit in a method for treating or preventing drug withdrawal symptoms or pain in a human or animal patient.

In yet another aspect, the present technology provides a composition comprising at least one conjugate of hydrocodone and at least one heteroaryl carboxylic acid, a derivative thereof, or a combination thereof.

In yet another aspect, the present technology provides at least one conjugate of hydrocodone and at least one heteroaryl carboxylic acid, a derivative thereof, or a combination thereof where at least one heteroaryl carboxylic acid is selected from formula II, formula III or formula IV, wherein formula II, formula III and formula IV are:

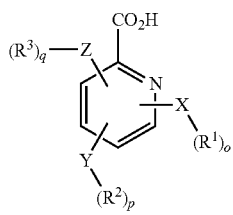
(II)

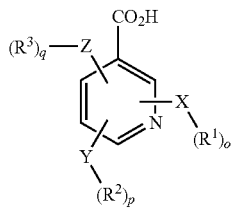
(III)

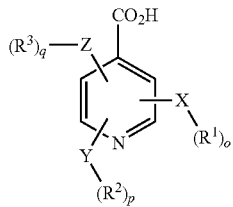
(IV)

wherein X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer from 1 to 10. In some aspects, at least one heteroaryl carboxylic acid is a pyridine derivative.

In some aspects, the present technology provides at least one conjugate that prevents drug tampering by either physical or chemical manipulation.

In another aspect, the present technology provides a method for treating a patient having a disease, disorder or condition requiring or mediated by binding of an opioid to the opioid receptors of the patient, comprising orally administering to the patient a pharmaceutically effective amount of at least one conjugate of hydrocodone and at least one heteroaryl carboxylic acid.

In a further aspect, the present technology provides a method for treating a patient having a disease, disorder or condition requiring or mediated by binding of an opioid to the opioid receptors of the patient, comprising orally administering to the patient a pharmaceutically effective amount of at least one conjugate of hydrocodone and at least one heteroaryl carboxylic acid, where the heteroaryl carboxylic acid is selected from formula II, formula III or formula IV, wherein formula II, formula III and formula IV are:

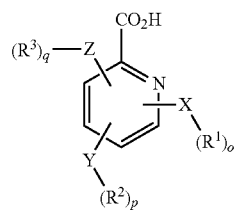
(II)

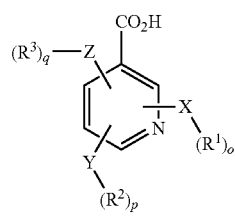
(III)

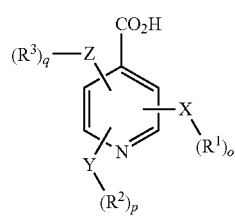
(IV)

where X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer from 1 to 10.

In another aspect, the present technology provides a method for treating a patient having a disease, disorder or condition requiring or mediated by binding of an opioid to the opioid receptors of the patient, comprising orally administering to the patient a pharmaceutically effective amount of at least one conjugate of hydrocodone and at least one nicotinic acid, a derivative thereof, or a combination thereof.

In another aspect, the present technology provides a method for treating a patient having a disease, disorder or condition requiring or mediated by inhibiting binding of an opioid to the opioid receptors of the patient, comprising orally administering to the patient a pharmaceutically effective amount of at least one conjugate of hydrocodone and at least one heteroaryl carboxylic acid. In some aspects, the heteroaryl carboxylic acid is selected from formula II, formula III or formula IV, wherein formula II, formula III and formula IV are:

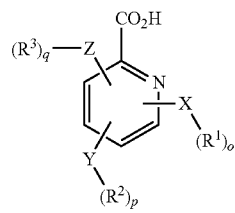
(II)

-continued

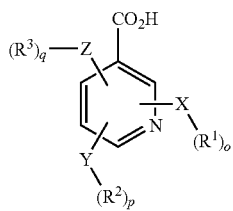

(III)

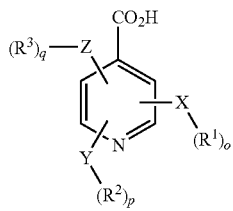

(IV)

wherein X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer from 1 to 10.

In another aspect, the present technology provides a method for treating a patient having a disease, disorder or condition requiring or mediated by inhibiting binding of an opioid to the opioid receptors of the patient, comprising orally administering to the patient a pharmaceutically effective amount of at least one conjugate of hydrocodone and at least one nicotinic acid, a derivative thereof, or a combination thereof.

In yet another aspect, the present technology provides a pharmaceutical kit including a specified number of individual doses in a package containing a pharmaceutically effective amount of at least one conjugate of hydrocodone and at least one heteroaryl carboxylic acid, a derivative thereof, or a combination thereof, wherein the heteroaryl carboxylic acid is selected from formula II, formula III or formula IV, wherein formula II, formula III and formula IV are:

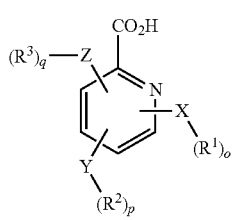

(II)

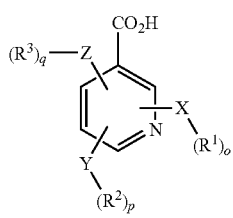

(III)

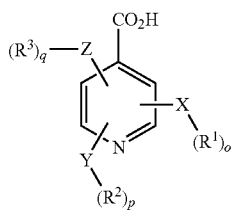

(IV)

wherein X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer from 1 to 10. In some aspects, the kit further comprises instructions for use of the kit in a method for treating or preventing drug withdrawal symptoms or pain in a human or animal patient.

In yet another aspect, the present technology provides a prodrug comprising at least one conjugate of hydrocodone and at least one benzoic acid or benzoic acid derivative, a salt thereof, or a combination thereof, the benzoic acid or benzoic acid derivative having the following formula I:

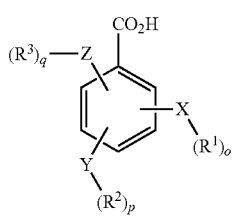

(I)

where X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer between 1 and 10.

In another aspect, the present technology provides a prodrug comprising at least one conjugate of hydrocodone and at least one benzoic acid, a derivative thereof, or a combination thereof.

In yet another aspect, the present technology provides a prodrug comprising at least one conjugate of hydrocodone and at least one heteroaryl carboxylic acid, a derivative thereof, or a combination thereof. In some aspects, the prodrug includes at least one heteroaryl carboxylic acid selected from formula II, formula III or formula IV, wherein formula II, formula III and formula IV are:

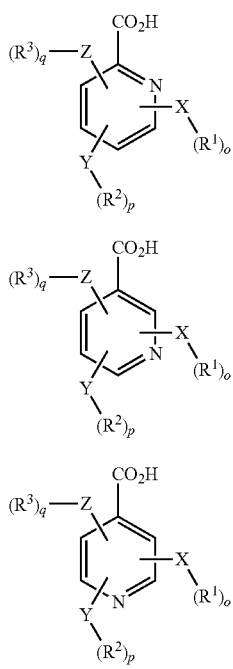

wherein X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer from 1 to 10.

In yet another aspect, the present technology provides a prodrug comprising at least one conjugate of hydrocodone and at least one nicotinic acid, a derivative thereof, or a combination thereof.

In some aspects, the prodrug includes an aminobenzoate, a hydroxybenzoate, an aminohydroxybenzoate, a derivative thereof, or combination thereof.

In some aspects, at least one conjugate binds reversibly to the opioid receptors of the patient. In some further aspects, at least one conjugate binds reversibly to the opioid receptors of the patient without a CNS depressive effect. In yet another aspect, at least one conjugate prevents or reduces at least one constipatory side effect of unconjugated hydrocodone.

BRIEF DESCRIPTION OF SEVERAL VIEWS OF THE DRAWINGS

FIG. 4. FIG. 4A is a Table of common hydrocodone products and dosage ranges and FIG. 4B is a Table of common hydrocodone products used in cough syrups.

FIG. 13. Synthesis diagrams of conjugates of hydrocodone. FIG. 13A depicts the synthesis of benzoate hydrocodone. FIG. 13B depicts the synthesis of nicotinate hydrocodone (nicotinic acid). FIG. 13C depicts the synthesis of 2-aminobenzoate hydrocodone. FIG. 13D depicts the synthesis of salicylate hydrocodone.

DETAILED DESCRIPTION OF THE INVENTION

Figure 1:
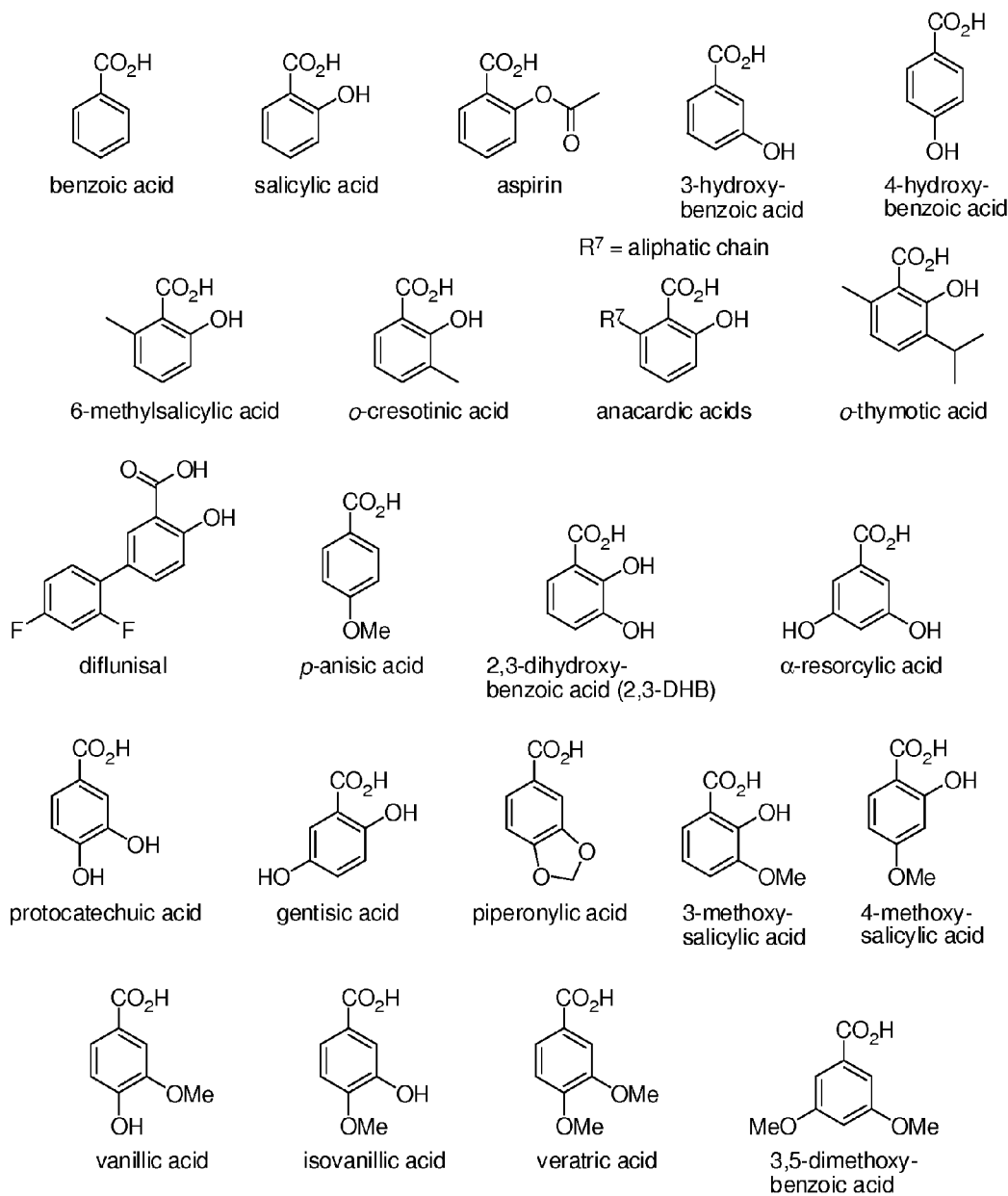
FIG. 1. Chemical structures of hydroxybenzoic acids and benzoic acid derivatives for use in the making of the conjugates of the present technology.
Figure 1:
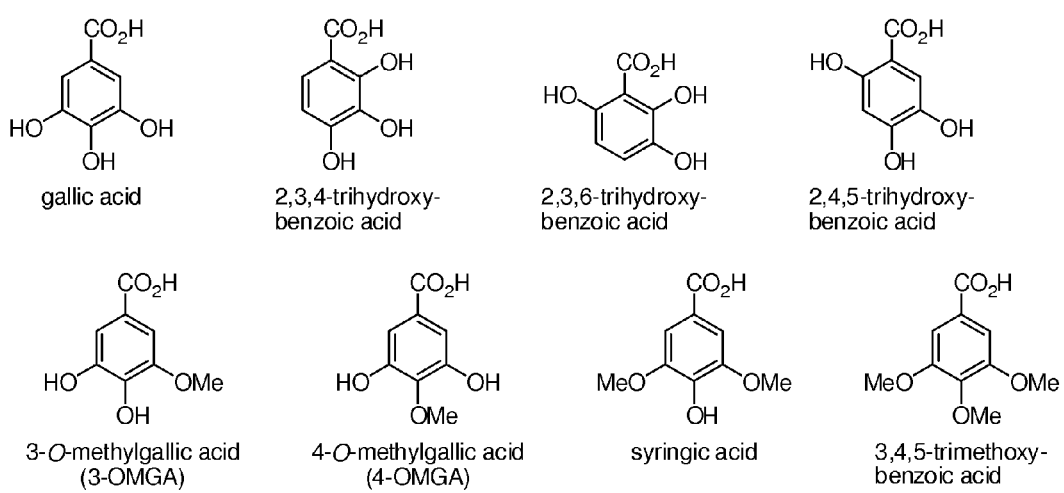

The present technology provides compositions comprising aryl carboxylic acids chemically conjugated to hydrocodone (morphinan-6-one, 4,5-alpha-epoxy-3-methoxy-17-methyl) to form novel prodrugs and compositions of hydrocodone. In some embodiments, the chemical bond between these two moieties can be established by reacting the C-6 enol tautomer of hydrocodone with the activated carboxylic acid function of an aryl carboxylic acid thereby creating an enol-ester conjugate.

The use of "opioid" is meant to include any drug that activates the opioid receptors found in the brain, spinal cord and gut. There are four broad classes of opioids: naturally occurring opium alkaloids, such as morphine (the prototypical opioid) codeine, and thebaine; endogenous opioid peptides, such as endorphins; semi-synthetics such as heroine, oxycodone and hydrocodone that are produced by modifying natural opium alkaloids (opiates) and have similar chemical structures; and pure synthetics such as fentanyl and methadone that are not produced from opium and may have very different chemical structures than the opium alkaloids. Additional examples of opioids are hydromorphone, oxymorphone, methadone, levorphanol, dihydrocodeine, meperidine, diphenoxylate, sufentanil, alfentanil, propoxyphene, pentazocine, nalbuphine, butorphanol, buprenorphine, meptazinol, dezocine, and pharmaceutically acceptable salts thereof.

The use of "hydrocodone" is meant to include a semisynthetic narcotic analgesic and antitussive prepared from codeine with multiple actions qualitatively similar to those of codeine. It is commonly used for the relief of moderate to moderately severe pain. Trade names include Anexsia™, Hycodan™, Hycomine™, Lorcet™, Lortab™, Norco™, Tussionex™, Tylox™, and Vicodin™. Other salt forms of hydrocodone, such as hydrocodone bitartrate and hydrocodone polistirex, are encompassed by the present technology.

Some embodiments of the present technology provide carboxylic acids conjugated to hydrocodone, where the carboxylic acid group is directly attached to the aryl moiety. Carboxylic acids directly attached to the aryl moiety include benzoates and heteroaryl carboxylic acids.

Some embodiments of the present technology provide at least one conjugate of hydrocodone and at least one benzoic acid or benzoic acid derivative, a salt thereof, or a combination thereof. Benzoates are common in nature and include, for example but are not limited to, aminobenzoates (e.g., anthranilic acid analogs such as fenamates), aminohydroxybenzoates and hydroxybenzoates (e.g., salicylic acid analogs).

The general structure of benzoic acid and benzoic acid derivatives of the present technology is:

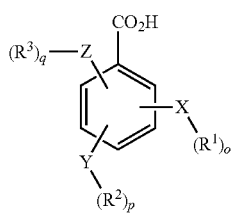

where X, Y and Z can be independently any combination of H, O, S, NH or —(CH$_2$)—; R$^1$, R$^2$ and R$^3$ can be independently any of the following: H, alkyl, alkoxy, aryl, alkenyl, alkynyl, halo, haloalkyl, alkylaryl, arylalkyl, heterocycle, arylalkoxy, cycloalkyl, cycloalkenyl or cycloalkynyl, and o, p, q can be independently either 0 or 1.

Suitable hydroxybenzoic acids can be found in FIG. 1 and include, but are not limited to, benzoic acid, salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflusinal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, 3,4,5-trimethoxybenzoic acid.

Figure 2:
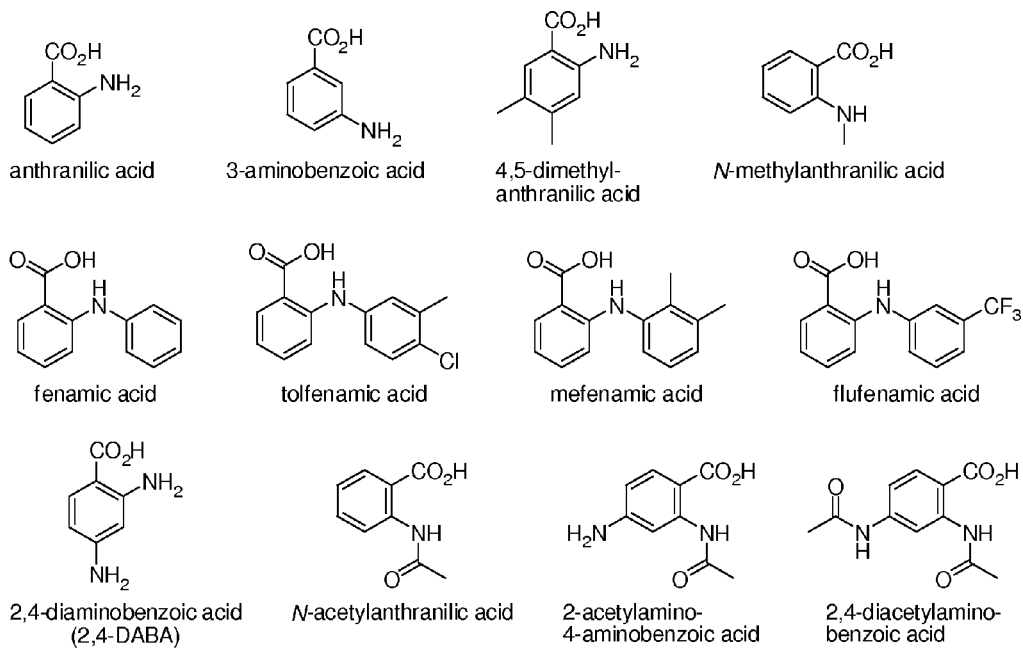
FIG. 2. Chemical structures of aminobenzoic acids for use in the making of the conjugates of the present technology.
Figure 3:
FIG. 3. Chemical structures of aminohydroxybenzoic acids for use in the making of conjugates of the present technology.

Suitable aminobenzoic acids are shown in FIG. 2 and include, but are not limited to, anthranilic acid, 3-aminobenzoic acid, 4,5-dimethylanthranilic acid, N-methylanthranilic acid, N-acetylanthranilic acid, fenamic acids (e.g., tolfenamic acid, mefenamic acid, flufenamic acid), 2,4-diaminobenzoic acid (2,4-DABA), 2-acetylamino-4-aminobenzoic acid, 4-acetylamino-2-aminobenzoic acid, 2,4-diacetylaminobenzoic acid.

Suitable aminohydroxybenzoic acids include, but are not limited to, 4-Aminosalicylic acid, 3-hydroxyanthranilic acid, 3-methoxyanthranilic acid.

In some embodiments, the composition includes a benzoate conjugate comprising at least one hydrocodone conjugated to at least one benzoic acid or benzoic acid derivative, salt thereof or combination thereof.

In some embodiments, the benzoates include numerous benzoic acid analogs, benzoate derivatives with hydroxyl or amino groups or a combination of both. The hydroxyl and amino functions may be present in their free form or capped with another chemical moiety, preferably but not limited to methyl or acetyl groups. The phenyl ring may have additional substituents, but the total number of substituents can be four or less, three or less, or two or less.

In another embodiment, the prodrug or conjugate composition of the present technology is benzoate-hydrocodone, which has the structure:

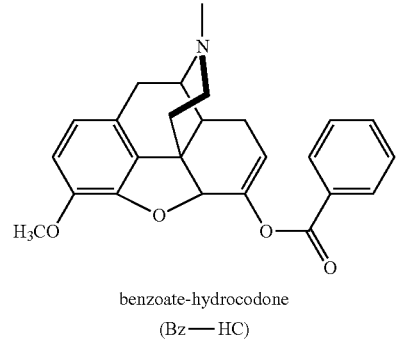

benzoate-hydrocodone
(Bz—HC)

In yet another embodiment, the present technology provides a prodrug or composition comprising at least one conjugate of hydrocodone and at least one heteroaryl carboxylic acid, a derivative thereof, or a combination thereof. The heteroaryl carboxylic acid can be selected from formula II, formula III or formula IV where formula II, formula III and formula IV are:

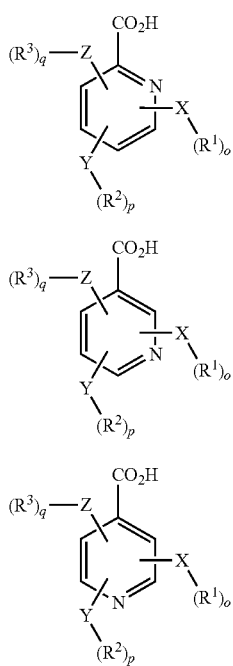

(II)

(III)

(IV)

For these formulas, X, Y and Z are independently selected from the group consisting of H, O, S, NH and —(CH$_2$)$_x$—; R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer from 1 to 10.

In some embodiments, the carboxy group of the aryl carboxylic acids can be attached directly to the aromatic ring. The present technology includes both carbon-only aryl groups and aryl groups with heteroatoms (heteroaryl). The aryl or heteroaryl group which is connected directly to the carboxyl function can be a 6-membered ring and contains no or one heteroatom. In some embodiments, the additional substituted or unsubstituted aromatic or aliphatic rings can be fused to this 6-membered aryl or heteroaryl moiety. In some embodiments, the aryl carboxylic acids may have only one free carboxylic acid group and the total number of phenyl substituents on the 6-membered ring should be four or less, for example, 4, 3, 2 or 1.

In some embodiments of the present technology, depending on the individual aryl carboxylic acid that is connected to hydrocodone, the conjugate of hydrocodone can have a neutral, free acid, free base, or various pharmaceutically acceptable anionic or cationic salt forms or salt mixtures with any ratio between positive and negative components. These salt forms include, but are not limited to: acetate, L-aspartate, besylate, bicarbonate, carbonate, D-camsylate, L-camsylate, citrate, edisylate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, D-tartrate, L-tartrate, D,L-tartrate, mesotartrate, benzoate, gluceptate, D-glucuronate, hybenzate, isethionate, malonate, methylsulfate, 2-napsylate, nicotinate, nitrate, orotate, stearate, tosylate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, and undecylenate.

For the present technology, a suitable conjugate of hydrocodone includes nicotinate-hydrocodone, which has the following structure:

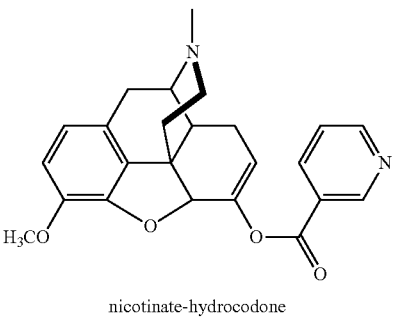

nicotinate-hydrocodone
(Nicotinate-HC)

Some embodiments of the present technology provide a conjugate of hydrocodone that is broken down in vivo either enzymatically or otherwise, releasing the active hydrocodone and the respective aryl carboxylic acid or metabolites thereof. The aryl carboxylic acids used in the conjugates of the present technology are non-toxic at the given dosing levels and are preferably known drugs, natural products, metabolites, or GRAS (Generally Regarded As Safe) compounds (e.g., preservatives, dyes, flavors, etc.) or non-toxic mimetics thereof.

Compounds, compositions and methods of the present technology provide reduced potential for overdose, reduced potential for abuse or addiction and/or improve hydrocodone's characteristics with regard to high toxicities or suboptimal release profiles. Without wishing to be limited to the below theory, the present inventors believe that overdose protection may occur due to the conjugates being exposed to different enzymes and/or metabolic pathways by oral administration where the conjugate is exposed through the gut and first-pass metabolism as opposed to exposure to enzymes in the circulation or mucosal membranes which limits the ability of the hydrocodone from being released from the conjugate. Therefore, abuse resistance is provided by limiting the "rush" or "high" available from the active hydrocodone released by the prodrug and limiting the effectiveness of alternative routes of administration.

The compositions of the present technology preferably have no or a substantially decreased pharmacological activity when administered through injection or intranasal routes of administration. However, they remain orally bioavailable. Again, not wanting to be bound by any particular theory, the bioavailability can be a result of the hydrolysis of the chemical linkage (i.e., a covalent linkage) following oral administration. In at least one embodiment, release of hydrocodone is reduced when the composition of the present technology is delivered by parenteral routes.

For example, in one embodiment, the composition of the present technology maintains its effectiveness and abuse resistance following the crushing of the tablet, capsule or other oral dosage form. In contrast, from parental non-conjugated (or "unconjugated") forms of hydrocodone, the hydrocodone is released immediately following crushing allowing the content of the crushed tablet to be used by injection or snorting producing the "rush" effect sought by addicts.

In some embodiments of the present technology, the conjugates of hydrocodone can be given orally to an animal or human patient, and, upon administration, release the active hydrocodone by being hydrolyzed in the body. Not to be bound by any particular theory, it is believed that since the aryl carboxylic acids are naturally occurring metabolites or mimetics thereof or pharmaceutically active compounds, these conjugates can be easily recognized by physiological systems resulting in hydrolysis and release of hydrocodone. The conjugates themselves have either no or limited pharmacological activity as a conjugate and consequently may follow a metabolic pathway that differs from the parent drug.

In some embodiments of the present technology, the choice of a suitable aryl carboxylic acids ("ligands") to conjugate to hydrocodone determines the release of hydrocodone into the systemic circulation and can be controlled even when the conjugate is administered via routes other than oral. In one embodiment, the modified hydrocodone would release hydrocodone similar to free or unmodified hydrocodone. In another embodiment, the conjugated hydrocodone releases hydrocodone in a controlled or sustained form. In some embodiments, this controlled release can alleviate certain side-effects and improve upon the safety profile of the parent drug. These side-effects may include, but are not limited to, anxiety, bruising, constipation, decreased appetite, difficulty breathing, dizziness, drowsiness, dry throat, diarrhea, headache, nausea, stomach cramps, stomach pain, vomiting. In another embodiment, the conjugated hydrocodone would selectively allow hydrocodone to be metabolized to hydromorphone. In some embodiments, these conjugates can be used for pain relief, such as moderate to severe pain relief.

Hydrocodone and other opioids are also highly addictive and prone to substance abuse. Recreational drug abuse of opioids is a common problem and usually begins with oral doses taken with the purpose of achieving euphoria ("rush", "high"). Over time the drug abuser often increases the oral dosages to attain more powerful "highs" or to compensate for heightened opioid tolerance. This behavior can escalate and result in exploring of other routes of administration such as intranasal ("snorting") and intravenous ("shooting").

In some embodiments of the present technology, the hydrocodone that is conjugated with a suitable aryl carboxylic acid ligand does not result in rapid spikes in plasma concentrations after oral administration that is sought by a potential drug abuser. In some embodiments, hydrocodone released from these conjugates has a delayed $T_{max}$ and possibly lower $C_{max}$ than the unconjugated hydrocodone. Not to be bound by any particular theory, it is believed that the conjugates of the present technology, when taken orally or by other non-oral routes, do not provide the feeling of a "rush" even when taken at higher doses but still maintain pain relief.

Additionally, in some embodiments, hydrocodone conjugated with appropriate ligands of the present technology is not hydrolyzed efficiently when administered via non-oral routes. As a result, these conjugates do not generate high plasma or blood concentrations of released hydrocodone when injected or snorted compared to free hydrocodone administered through these routes.

In some embodiments, the conjugates of the present technology, since they consist of covalently bound hydrocodone, are not able to be physically manipulated to release the hydrocodone opioid from the conjugated hydrocodone by methods, for example, of grinding up or crushing of solid forms. Further, the conjugates of the present technology exhibits resistance to chemical hydrolysis under conditions a potential drug abuser may apply to "extract" the active portion of the molecule, for example, by boiling, or acidic or basic solution treatment of the conjugate.

The compositions and prodrugs of the present technology can be oral dosage forms. These dosage forms include but are not limited to tablet, capsule, caplet, troche, lozenge, powder, suspension, syrup, solution or oral thin film (OTF). Preferred oral administration forms are capsule, tablet, solutions and OTF.

Solid dosage forms can include, but are not limited to, the following types of excipients: antiadherents, binders, coatings, disintegrants, fillers, flavors and colors, glidants, lubricants, preservatives, sorbents and sweeteners.

Oral formulations of the present technology can also be included in a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow.

Soft gel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The individual units so formed are then dried to constant weight.

Chewable tablets, for example, may be prepared by mixing the formulations with excipients designed to form a relatively soft, flavored, tablet dosage form that is intended to be chewed rather than swallowed. Conventional tablet machinery and procedures, for example, direct compression and granulation, i.e., or slugging, before compression, can be utilized. Those individuals involved in pharmaceutical solid dosage form production are versed in the processes and the machinery used, as the chewable dosage form is a very common dosage form in the pharmaceutical industry.

Film coated tablets, for example may be prepared by coating tablets using techniques such as rotating pan coating methods or air suspension methods to deposit a contiguous film layer on a tablet.

Compressed tablets, for example may be prepared by mixing the formulation with excipients intended to add binding qualities to disintegration qualities. The mixture is either directly compressed or granulated then compressed using methods and machinery known to those in the industry. The resultant compressed tablet dosage units are then packaged according to market need, for example, in unit dose, rolls, bulk bottles, blister packs, etc.

The present technology also contemplates the use of biologically-acceptable carriers which may be prepared from a wide range of materials. Without being limited to, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons working in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

It should be understood that in addition to the ingredients particularly mentioned above, the formulations of the present technology can include other suitable agents such as flavoring agents, preservatives and antioxidants. Such antioxidants would be food acceptable and could include vitamin E, carotene, BHT or other antioxidants.

Other compounds which may be included by admixture are, for example, medically inert ingredients, e.g., solid and liquid diluents, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulfates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. In particular a syrup for diabetic patients can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose or polyvinyl alcohol.

Current approved formulations of hydrocodone are combination therapies of hydrocodone and one or more other non-narcotic active ingredient depending on intended indication. Examples of these active pharmaceuticals include, but are not limited to, acetaminophen, phenylpropanolamine, homatropine, ibuprofen, aspirin, pheniramine, chlorpheniramine, phenylephrine, pseudoephedrine, pyrilamine and guaifenesin. The conjugated hydrocodone of the present technology can be formulated with one or a combination of these or other active substances or as standalone active ingredient without any other actives.

The conjugate compositions or prodrugs may be used in methods of treating a patient having a disease, disorder or condition requiring or mediated by binding or inhibiting binding of an opioid to the opioid receptors of the patient. Treatment comprises orally administering to the patient a pharmaceutically effective amount of at least one conjugate of hydrocodone as described in the present technology. The conjugate can exhibit a slower rate of release over time and AUC when compared to an equivalent molar amount of unconjugated hydrocodone. In other embodiments, at least one conjugate can exhibit less variability in the oral PK profile when compared to unconjugated hydrocodone.

In other embodiments, at least one conjugate is provided in an amount sufficient to provide a therapeutically bioequivalent AUC (area under the curve) when compared to a molar equivalent amount of unconjugated hydrocodone. In further embodiments, the conjugate is provided in an amount sufficient to provide a therapeutically bioequivalent AUC when compared to unconjugated hydrocodone but has a lower $C_{max}$ (peak concentration) in plasma or does not provide an equivalent $C_{max}$ in plasma concentrations. In some aspects, the conjugate is provided in an amount sufficient to provide a therapeutically bioequivalent $C_{max}$ when compared to unconjugated hydrocodone.

Suitable diseases, disorders or conditions that can be treated by the prodrugs or compositions of the present technology are narcotic addiction or drug addiction and/or acute or chronic pain.

Dosages for the conjugates of the present technology depend on their molecular weight and the respective weight-percentage of hydrocodone as part of the whole conjugate, and therefore can be higher than the dosages of free hydrocodone. Dosages can be calculated based on the strengths of dosages of hydrocodone bitartrate which range between 2.5 mg and 15 mg per dose. Dose conversion from hydrocodone bitartrate to hydrocodone prodrug can be performed using the following formula:

dose(HC prodrug/conjugate)=[dose(HC bitartrate)×
(molecular weight(HC prodrug/conjugate)/
494.49)]/proportion of hydrocodone released
from prodrug/conjugate HC: Hydrocodone Suitable dosages of the conjugated hydrocodone of the present technology include, but are not limited to, formulations including from about 0.5 mg or higher, alternatively from about 2.5 mg or higher, alternatively from about 5.0 mg or higher, alternatively from about 7.5 mg or higher, alternatively from about 10 mg or higher, alternatively from about 20 mg or higher, alternatively from about 30 mg or higher, alternatively from about 40 mg or higher, alternatively from about 50 mg or higher, alternatively from about 60 mg or higher, alternatively from about 70 mg or higher, alternatively from about 80 mg or higher, alternatively from about 90 mg or higher, alternatively from about 100 mg or higher, and include any additional increments thereof, for example, 0.1, 0.2, 0.25, 0.3, 0.4, 0.5, 0.6, 0.7, 0.75, 0.8, 0.9 or 1.0 mg and multiplied factors thereof, (e.g., ×1, ×2, ×2.5, ×5, ×10, ×100, etc). The present technology also includes dosage formulations including currently approved formulations of hydrocodone (See FIG. 4), where the dosage can be calculated using the above-noted formula determined by the amount of hydrocodone bitartrate. The present technology provides for dosage forms formulated as a single therapy or as a combination therapy with other API's (FIG. 4).

The conjugates of hydrocodone with derivatives of benzoic acid or nicotinic acid of the present technology have a number of advantages including, but not limited to, a reduced patient variability of plasma concentrations of hydrocodone or hydromorphone when compared to free hydrocodone, reduced drug abuse potential, reduced risk of chemical or physical manipulation resulting in full dosage of hydrocodone released, improved dosage forms through covalent linkage to carboxylic acids or derivatives thereof, increased or decreased metabolism of hydrocodone to hydromorphone and/or decreased side-effects other than drug abuse.

Hydrocodone is a narcotic analgesic, which acts as weak agonist at opioid receptors in the central nervous system (CNS). It primarily affects the μ (mu) receptor (OP3), but also exhibits agonist activity at the δ (delta) receptor (OP1) and κ (kappa) receptor (OP2). Additionally, hydrocodone displays antitussive properties by suppressing the cough reflex in the medullary cough center of the brain.

Side effects of opioid analgesics include gastrointestinal dysfunction caused by the opioids binding to the mu (μ) receptors present in the gastrointestinal tract. The side-effects in the stomach include a reduction in the secretion of hydrochloric acid, decreased gastric motility, thus prolonging gastric emptying time, which can result in esophageal reflux. Passage of the gastric contents through the duodenum may be delayed by as much as 12 hours, and the absorption of orally administered drugs is retarded. In the small intestines the opioid analgesics diminish biliary, pancreatic and intestinal secretions and delay digestion of food in the small intestine. Propulsive peristaltic waves in the colon are diminished or abolished after administration of opioids, and tone is increased to the point of spasm. The resulting delay in the passage of bowel contents causes considerable desiccation of the feces, which, in turn retards their advance through the colon. These actions, combined with inattention to the normal sensory stimuli for defecation reflex due to the central actions of the drug, contribute to opioid-induced constipation.

Hydrocodone is used for the treatment of moderate to moderately severe pain and for inhibition of cough (especially dry, nonproductive cough). The prodrugs of the present technology may be administered for the relief of pain or cough depression or for the treatment of any condition that may require the blocking of opioid receptors.

The conjugates of the present technology can provide a decrease in side effects of the opioid analgesic, including reduced or inhibited constipatory effects.

The present technology also provides a method of synthesis for the preparation of the conjugated hydrocodone of the present technology. In one embodiment, the synthesis of the present technology includes the steps of:
1. Protection of the ligand, if necessary;
2. Activation of the ligand carboxylic acid group, if not already in activated form;
3. Addition of the activated ligand to hydrocodone or vice versa in the presence of base; and
4. Removal of ligand protecting groups, if applicable.

If the aryl carboxylic acid contains any additional reactive functional groups that may interfere with the coupling to hydrocodone, it may be necessary to first attach one or more protecting groups. Any suitable protecting group may be used depending on the type of functional group and reaction conditions. Some protecting group examples are: acetyl (Ac), β-methoxyethoxymethyl ether (MEM), methoxymethyl ether (MOM), p-methoxybenzyl ether (PMB), trimethylsilyl (TMS), tert.-butyldimethylsilyl (TBDPS), triisopropylsilyl (TIPS), carbobenzyloxy (Cbz), p-methoxybenzyl carbonyl (Moz), tert.-butyloxycarbonyl (Boc), 9-fluorenylmethyloxycarbonyl (Fmoc), benzyl (Bn), p-methoxybenzyl (MPM), tosyl (Ts). Temporary formation of acetals or ketals from carbonyl functions may also be appropriate.

The carboxylic acid group of the ligands should be activated in order to react with hydrocodone and to generate appreciable amounts of conjugate. This activation can be accomplished in numerous ways by a variety of coupling agents known to one skilled in the art. Examples of such coupling agents are: N,N-dicyclohexylcarbodiimide (DCC), N-(3-dimethylaminopropyl)-N-ethylcarbodiimide (EDCI), N,N'-diisopropylcarbodiimide (DIC), 1,1'-carbonyldiimidazole (CDI) or other carbodiimides; (benzotriazol-1-yloxy)tris(dimethylamino)phosphonium hexafluorophosphate (BOP), bromotripyrrolidinophosphonium hexafluorophosphate (Py-BroP), (benzotriazol-1-yloxy)tripyrrolidinophosphonium hexafluorophosphate (PyBOP) or other phosphonium-based reagents; O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), fluoro-N,N,N',N'-tetramethylformamidinium hexafluorophosphate (TFFH), N,N,N',N'-tetramethyl-O—(N-succinimidyl)uronium tetrafluoroborate (TSTU) or other aminium-based reagents. The aryl carboxylic acid can also be converted to a suitable acyl halide, acyl azide or mixed anhydride.

A base may be required at any step in the synthetic scheme of an aryl carboxylic acid conjugate of hydrocodone. Suitable bases include but are not limited to: 4-methylmorpholine (NMM), 4-(dimethylamino)pyridine (DMAP), N,N-diisopropylethylamine, lithium bis(trimethylsilyl)amide, lithium diisopropylamide (LDA), any alkali metal tert.-butoxide (e.g., potassium tert.-butoxide), any alkali metal hydride (e.g., sodium hydride), any alkali metal alkoxide (e.g., sodium methoxide), triethylamine or any other tertiary amine.

Suitable solvents that can be used for any reaction in the synthetic scheme of an aryl carboxylic acid conjugate of hydrocodone include but are not limited to: acetone, acetonitrile, butanol, chloroform, dichloromethane, dimethylformamide (DMF), dimethylsulfoxide (DMSO), dioxane, ethanol, ethyl acetate, diethyl ether, heptane, hexane, methanol, methyl tert.-butyl ether (MTBE), isopropanol, isopropyl acetate, diisopropyl ether, tetrahydrofuran, toluene, xylene or water.

In some embodiments, the prodrug is hydrophobic and thus poorly water soluble. This results in a gel-like consistency or clumpy suspension when the compound is mixed with water. Examples of these prodrugs include, but are not limited to, Piperonylate-HC, 3-OH-4-MeO-Bz-HC, 3-OH-Bz-HC and Gallate-HC. These prodrugs cannot be dosed intranasally in rats due to their lack of water solubility. Not to be bound by any theory, it is assumed that these compounds would also congeal or become clumpy when a human subject tries to inhale them intranasally ("snorting"). This property would not only make an attempt of intranasal abuse an unpleasant experience but would likely also prevent the prodrug from permeating the nose mucosa. As a consequence, these compounds become ineffective for this route of administration.

The present technology provides pharmaceutical kits for the treatment or prevention of drug withdrawal symptoms or pain in a patient. The patient may be a human or animal patient. Suitable human patients include pediatric patients, geriatric (elderly) patients, and normative patients. The kit comprises a specific amount of the individual doses in a package containing a pharmaceutically effective amount of at least one conjugate of hydrocodone of the present technology. The kit can further include instructions for use of the kit. The specified amount of individual doses may contain from about 1 to about 100 individual dosages, alternatively from about 1 to about 60 individual dosages, alternatively from about 10 to about 30 individual dosages, including, about 1, about 2, about 5, about 10, about 15, about 20, about 25, about 30, about 35, about 40, about 45, about 50, about 55, about 60, about 70, about 80, about 100, and include any additional increments thereof, for example, 1, 2, 5, 10 and multiplied factors thereof, (e.g., ×1, ×2, ×2.5, ×5, ×10, ×100, etc).

The presently described technology and its advantages will be better understood by reference to the following examples. These examples are provided to describe specific embodiments of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Example 1

Chemical Stability of Benzoate and Heteroaryl Carboxylate Conjugates of Hydrocodone Exemplary conjugates of hydrocodone of the present technology and control test conjugates not of the present technology were tested for chemical stability under conditions similar to what a potential drug abuser may use to "extract" the active portion of the molecule, for example dissolved in water, hydrochloric acid or sodium bicarbonate either at ambient temperature or 100° C. The conjugates were placed in a solution of water at either ambient temperature (about 20° C.) or in an oil bath at 100° C. for one hour and the amount of the conjugate that was hydrolyzed under these conditions was measured. Table 1 demonstrates the results, showing that the conjugates did not release hydrocodone at ambient temperature or when heated in water to 100° C. for one hour.

TABLE 1

| Compound | water[a] | |
|---|---|---|
| | ambient | 100° C. |
| 4-OH—Bz—HC | 0% | 0% |
| 2-Abz-HC | 0% | 0% |
| 4-MeO—Bz—HC | 0% | 0% |

Further, samples of conjugates of hydrocodone of the present technology were tested and compared with samples of other conjugates not of the present technology of hydrocodone (Adipate-HC) for their hydrolysis to hydrocodone after dilution in 1 N hydrochloric acid (HCl) for 1 hour at ambient temperature (~20° C.) or in an oil bath at 100° C. The percentages indicate how much of the initial amount of conjugate was hydrolyzed under these conditions. The results are shown in Table 2.

TABLE 2

| Compound | %-release in 1N HCl[a] | |
|---|---|---|
| | ambient | 100° C. |
| 4-OH—Bz—HC | 0% | 30% |
| 2-Abz-HC | 0% | 16% |
| 3-OH—4-MeO—Bz—HC | 0% | 35% |
| 2-OH—Bz—HC | 3% | 27% |
| Adipate-HC | 13% | 100% |

Samples of each conjugate were dissolved in a solution of 5% $NaHCO_3$ for one hour at either ambient temperature (~20° C.) or in an oil bath at 100° C. The percentages indicate how much of the initial amount of conjugate was hydrolyzed under these conditions as shown in Table 3 for the conjugates of the present technology and comparison conjugates not of the present technology (Tyr-Tyr-Phe-Phe-Ile-Hydrocodone (YYFFI-HC) or Adipiate-HC).

TABLE 3

| Compound | %-release in 5% $NaHCO_3$[a] | |
|---|---|---|
| | ambient | 100° C. |
| 4-OH—Bz—HC | 1% | 23% |
| 3-OH—4-MeO—Bz—HC | 0% | 36% |
| YYFFI-HC | 0% | 70% |
| Adipate-HC | 3% | 100% |

Example 2

Oral PK Profiles of Conjugated Hydrocodone of the Present Technology

Figure 5:
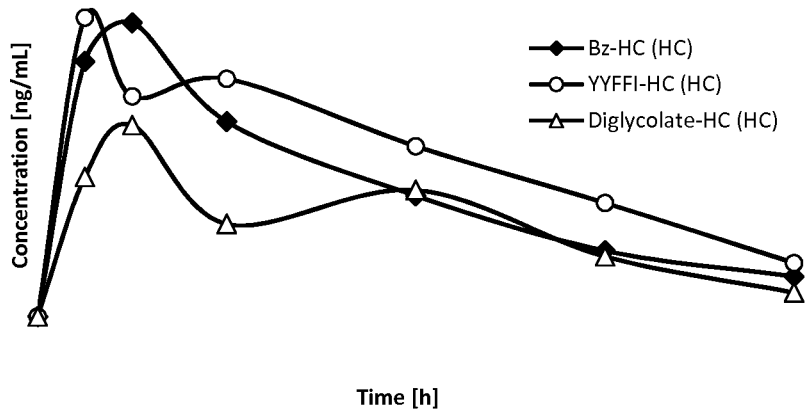
FIG. 5. PK profile graph of plasma concentrations of hydrocodone released from Bz-HC (benzoate-hydrocodone), YYFFI-HC (Tyr-Tyr-Phe-Phe-Ile-Hydrocodone) and Diglycolate-HC over time upon oral administration in rats.
Figure 6:
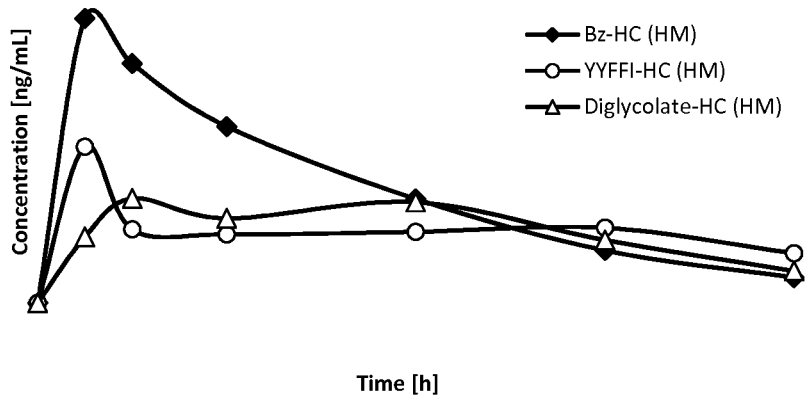
FIG. 6. PK profile graph of plasma concentrations of active metabolite hydromorphone over time upon oral administration of Bz-HC, YYFFI-HC, and Diglycolate-HC in rats.

Oral PK curves were determined for benzoate-hydrocodone (Bz-HC), a prodrug of the present technology, as compared to two conjugates not within the scope of the present technology: YYFFI-HC and Diglycolate-HC. Rats were orally administered an amount of the conjugate equivalent to 2 mg/kg of freebase hydrocodone and the plasma concentrations of released hydrocodone and of the active metabolite hydromorphone were measured over time by LC-MS/MS. As shown in FIG. 5, the oral PK curves for released hydrocodone were somewhat similar for Bz-HC and YYFFI-HC, but hydrocodone plasma concentrations produced by Bz-HC were mostly significantly higher than hydrocodone concentrations generated by Diglycolate-HC (AUC and $C_{max}$ for Bz-HC were approximately 40% and 50% higher, respectively). Additionally, Bz-HC created higher plasma concentrations of the more potent active metabolite hydromorphone (FIG. 6) than both, YYFFI-HC (AUC and $C_{max}$ for hydromorphone released from Bz-HC were approximately 60% and 80% higher, respectively) and Diglycolate-HC (AUC and $C_{max}$ for hydromorphone released from Bz-HC were approximately 55% and 180% higher, respectively). This suggests that all three compounds undergo a different metabolic pathway and that Bz-HC would have pain relieving effects potentially greater than either example.

Example 3

Intranasal PK Profile of Conjugates of Hydrocodone

Figure 7:
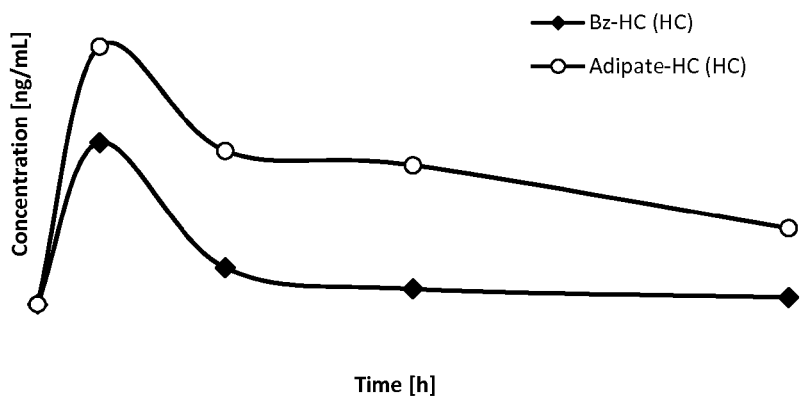
FIG. 7. PK profile graph of plasma concentrations of hydrocodone released from Bz-HC and Adipate-HC over time upon intranasal administration in rats.
Figure 8:
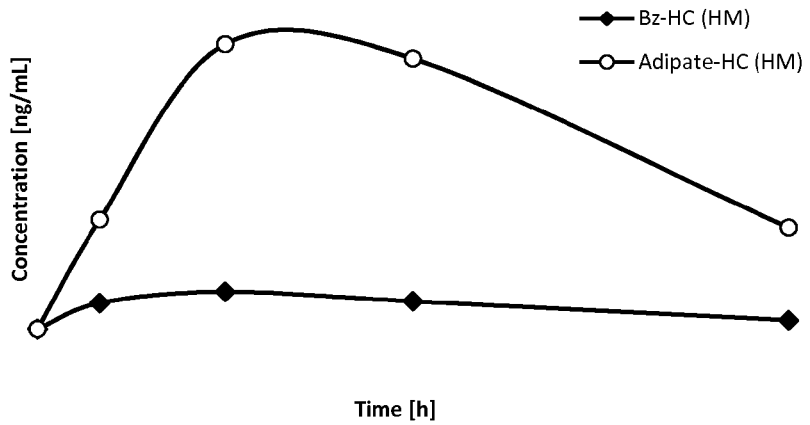
FIG. 8. PK profile graph of plasma concentrations of active metabolite hydromorphone over time upon intranasal administration of Bz-HC and Adipate-HC in rats.

Conjugates of hydrocodone of the present technology were tested for abuse resistance capabilities by examining the efficiency of a hydrolysis when administered via routes other than oral. Rats were intranasally treated with conjugate in an amount equivalent to 2 mg/kg of hydrocodone freebase and the concentration of released hydrocodone and of the active metabolite hydromorphone in the plasma of the rat were measured over time by LC-MS/MS. Hydrocodone plasma concentrations were significantly lower for Bz-HC (AUC and $C_{max}$ for hydromorphone released from Adipate-HC were approximately 280% and 60% higher, respectively) as shown in FIG. 7. Moreover, Bz-HC produced very low plasma concentration of hydromorphone when compared to Adipate-HC (AUC and $C_{max}$ for hydromorphone released from Adipate-HC were approximately 750% and 660% higher, respectively) as shown in FIG. 8.

Prodrugs of the present technology provide hydrocodone and hydromorphone plasma concentrations that are significantly lower than respective plasma concentration for unbound Hydrocodone-BT or for other prodrug classes when administered intranasally.

Example 4

Exemplary Intravenous PK Profiles of Conjugates of the Present Technology

The conjugates of hydrocodone of the present technology are hydrophobic, for example, Bz-HC, Nicotinate-HC, 4-MeO-Bz-HC, Piperonylate-HC, 4-OH-Bz-HC, Salicylate-HC, 3-OH-4-MeO-Bz-HC, 3-OH-Bz-HC and Gallate-HC. Therefore, these compounds cannot be administered intravenously at oral equivalent doses because they do not dissolve in a practical amount of water since injectable compounds must be completely in solution, because any solid particle may cause an embolism. The amount of water necessary to dissolve a desirable amount of conjugate would make an injection unfeasible and thus the present compositions and prodrugs have anti-abuse potential as opposed to other hydrocodone conjugates that are water soluble, such as Adipate-HC and Diglycolate-HC which can be administered intravenously at oral equivalent doses.

Example 5

Comparison of Oral PK Profiles of Conjugates of Hydrocodone

Figure 9:
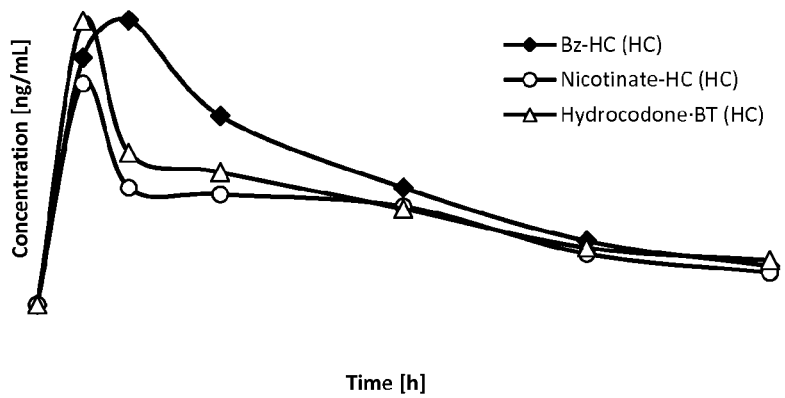
FIG. 9. PK profile graph of plasma concentrations of hydrocodone released from Bz-HC, Nicotinate-HC and Hydrocodone•BT over time upon oral administration in rats.
Figure 10:
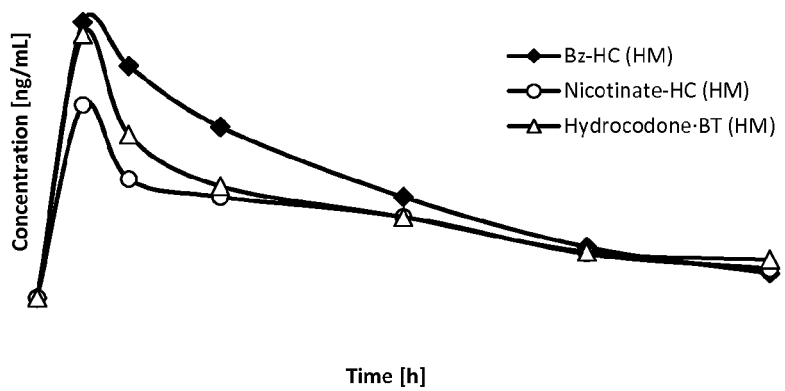
FIG. 10. PK profile graph of plasma concentrations of active metabolite hydromorphone over time upon oral administration of Bz-HC, Nicotinate-HC and Hydrocodone•BT in rats.

The plasma concentrations of hydrocodone released from Bz-HC and Nicotinate-HC were compared to plasma concentrations of hydrocodone generated by unconjugated Hydrocodone•BT after oral administration to rats. Rats were treated with conjugate or unconjugated drug in an amount equivalent to 2 mg/kg of hydrocodone freebase and the plasma concentration of hydrocodone or hydromorphone was measured by LC-MS/MS as demonstrated in FIGS. 9 and 10 respectively. The oral plasma concentration of hydrocodone released from Bz-HC increased similarly to the hydrocodone plasma concentrations observed with Hydrocodone•BT, until it reached $C_{max}$ ($C_{max}$ was approximately equal for both compounds). After $T_{max}$, the hydrocodone plasma concentration for Bz-HC decreased in a slower and more controlled fashion than for unconjugated Hydrocodone•BT (FIG. 9 and FIG. 10). Bz-HC had a higher AUC (AUC was approximately 25% higher, FIG. 9) when compared to Hydrocodone•BT and similar results were observed for the plasma concentrations of the active metabolite hydromorphone (FIG. 10).

Nicotinate-HC, produced hydrocodone and hydromorphone plasma concentrations that were below the respective concentrations found for unconjugated Hydrocodone•BT. The corresponding AUC values, however, were within the range of bioequivalence for the same dose (based on hydrocodone freebase).

Figure 11:
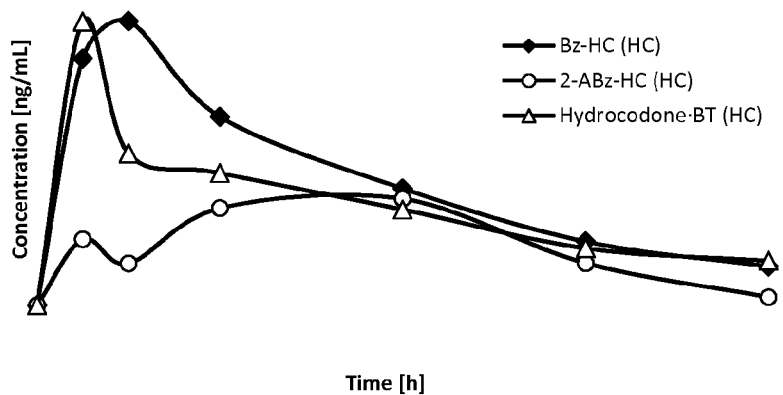
FIG. 11. PK profile graph of plasma concentrations of hydrocodone released from Bz-HC, 2-ABz-HC and Hydrocodone•BT over time upon oral administration in rats.
Figure 12:
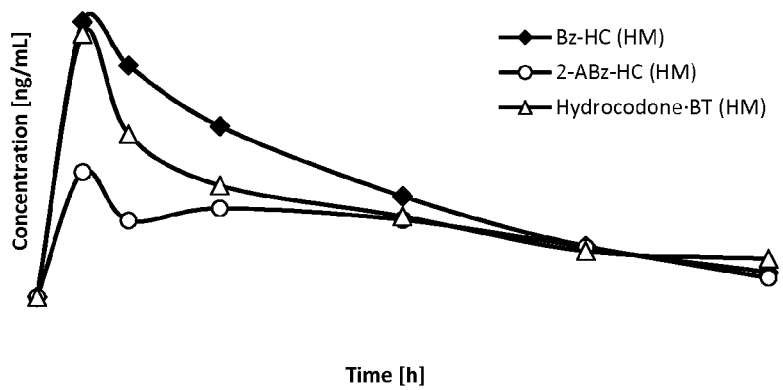
FIG. 12. PK profile graph of plasma concentrations of active metabolite hydromorphone over time upon oral administration of Bz-HC, 2-ABz-HC and Hydrocodone•BT in rats.

2-ABz-HC demonstrated a different release profile after oral administration to rats than Bz-HC or the unconjugated drug Hydrocodone•BT. Rats were treated with an amount equivalent to 2 mg/kg of hydrocodone freebase and the plasma concentration of hydrocodone or hydromorphone was measured by LC-MS/MS over time as shown in FIG. 11 or FIG. 12 respectively. 2-ABz-HC released hydrocodone very slowly indicated by a gradual increase of plasma concentration followed by an attenuated decrease (FIG. 11). This resulted in a flattened PK curve when compared with Hydrocodone•BT ($T_{max}$ for 2-ABz-HC was approximately four times longer, AUC and $C_{max}$ were approximately 35% and 60% lower, respectively). Overall, the PK curve of hydromorphone was also flatter for 2-ABz-HC than for Hydrocodone. BT (FIG. 12) but did show a small initial spike (AUC and $C_{max}$ for 2-ABz-HC were approximately 25% and 50% lower, respectively).

Example 6

Determination of Variation in Plasma Concentrations of Benzoate-Hydrocodone

To determine the variability of the plasma concentration of hydrocodone (HC) and hydromorphone (HM), the coefficient of variation (CV) was calculated for individual animals that were dosed with an amount equivalent to 2 mg/kg of hydrocodone freebase of benzoate-hydrocodone or the unconjugated hydrocodone bitartrate (BT) and the plasma concentrations of hydrocodone and hydromorphone were measured by LC-MS/MS over time. The CV was calculated by dividing the standard deviation of plasma concentrations in individual animals by the mean plasma concentrations of all dosed animals for a given time point. The "average CV" is the mean CV for all time points, as shown in Table 4.

TABLE 4

| Compound | Average $CV^a$ | |
| --- | --- | --- |
|  | HC | HM |
| Bz—HC | 46 | 41 |
| Hydrocodone•BT | 75 | 64 |

The lower average CV for Bz-HC indicates that this prodrug has lower relative variability in plasma concentrations of hydrocodone and hydromorphone across all dosed animals and time points than the unconjugated drug, hydrocodone bitartrate.

Example 7

Synthesis of Conjugates of Hydrocodone

Synthesis of Benzoate-Hydrocodone Freebase

To a solution of hydrocodone freebase (0.596 g, 1.99 mmol) in tetrahydrofuran (25 mL) was added 1 M LiN(SiMe$_3$)$_2$ in tetrahydrofuran (5.98 mL). The resulting orange suspension was stirred at ambient temperatures for 30 min. after which benzoate-succinic ester (1.25 g, 5.98 mmol) was added. The resulting mixture was stirred overnight at ambient temperatures and was quenched after 18 h by the addition of 100 mL saturated ammonium chloride solution which was allowed to stir for another 2 h. Ethyl acetate (100 mL) was added to the mixture and washed with saturated ammonium chloride solution (3×100 mL) and water (1×100 mL). Organic extracts were dried over anhydrous MgSO$_4$, solvent was removed and residue was taken up in 2-isopropanol (50 mL). Water was added until a solid formed. The resulting mixture was chilled, filtered and dried to obtain benzoate-hydrocodone freebase (0.333 g, 0.826 mmol, 42% yield) as a dark brown solid. This synthesis is depicted in FIG. 13A.

Synthesis of 2-Boc-Aminobenzoic Succinate:

2-Boc-aminobenzoic acid (2.56 g, 10.8 mmol) and N-hydroxy succinimide (1.37 g, 11.88 mmol) were dissolved in 25 mL of THF. DCC (2.45 g, 11.88 mmol) was added in one portion. The reaction was stirred overnight. The solid was filtered off and rinsed with acetone (2×10 mL). The filtrate was concentrated to dryness and dissolved in 100 mL of acetone. The resulting precipitate (DCU) was filtered off and the filtrate was concentrated to give a solid, which was collected and rinsed with methanol (3×4 mL) to yield 3.26 g (90%) of white product.

Synthesis of 2-Boc-Aminobenzoic Acid Ester of Hydrocodone:

To hydrocodone freebase (0.449 g, 1.5 mmol) dissolved in 20 mL of anhydrous THF was added a solution of LiHMDS in THF (1 M, 4.5 mL, 4.5 mmol) over 20 min. The mixture was stirred for 30 min. and 2-Boc-aminobenzoic succinate (1.50 g, 4.5 mmol) was added in one portion. The reaction was stirred for 4 hr and subsequently quenched with 100 mL of sat. $NH_4Cl$. The mixture was stirred for 1 hr. and extracted with 200 mL of ethyl acetate. The ethyl acetate layer was washed with sat. $NaHCO_3$ (2×80 mL) and 5% brine (80 mL), dried over anhydrous $Na_2SO_4$ and concentrated. The residue was purified by silica gel column chromatography (7% $MeOH/CH_2Cl_2$) to give 449 mg (58%) of an amorphous solid.

Synthesis of 2-Aminobenzoic Acid Ester of Hydrocodone Dihydrochloride Salt:

2-Boc-aminobenzoic acid ester of hydrocodone (259 mg, 0.5 mmol) was stirred in 4 mL of 4 N HCl/dioxane for 4 hr. The solvent was evaporated to dryness and to the residue was added 5 mL of ethyl acetate. The solid was collected and rinsed with ethyl acetate to give 207 mg (84%) of product.

Synthesis of 2-MOM-Salicylic Succinate:

2-MOM-salicylic acid (3.2 g, 17.6 mmol) and N-hydroxysuccinimide (2.23 g, 19.36 mmol) were dissolved in 40 mL of THF. DCC (3.99 g, 19.36 mmol) was added in one portion. The reaction was stirred overnight. The solid was filtered off and rinsed with acetone (2×10 mL). The filtrate was concentrated and the residue was recrystallized from 10 mL of methanol to give 2.60 g (53%) of a white solid.

Synthesis of 2-MOM-Salicylic Acid Ester of Hydrocodone:

To hydrocodone freebase (0.449 g, 1.5 mmol) dissolved in 20 mL of anhydrous THF was added a solution of LiHMDS in THF (1 M, 4.5 mL, 4.5 mmol) over 20 min. The mixture was stirred for 30 min. and 2-MOM-salicylic succinate (1.26 g, 4.5 mmol) was added in one portion. The reaction was stirred for 4 hr. and subsequently quenched with 100 mL of sat. $NH_4Cl$. The mixture was stirred for 1 hr. and extracted with 200 mL of ethyl acetate. The ethyl acetate layer was washed with sat. $NaHCO_3$ (2×80 mL) and 5% brine (80 mL), dried over anhydrous $Na_2SO_4$ and concentrated. The residue was purified by silica gel column chromatography (8% MeOH/$CH_2Cl_2$) to give 381 mg (58%) of a syrup.

Synthesis of Salicylic Acid Ester of Hydrocodone Hydrochloride Salt:

To 2-MOM-salicylic acid ester of hydrocodone (380 mg, 0.82 mmol) in 12 mL of methanol was added 0.5 mL of conc. HCl (12 N). The reaction was stirred for 6 hr. The solution was concentrated and residual water was removed by coevaporating with methanol (5×5 mL). The resulting residue was dissolved in 1 mL of methanol followed by 20 mL of ethyl acetate. The cloudy mixture was evaporated to about 4 mL. The resulting solid was collected and rinsed with ethyl acetate to yield 152 mg (41%) of product.

Example 8

Figure 14:
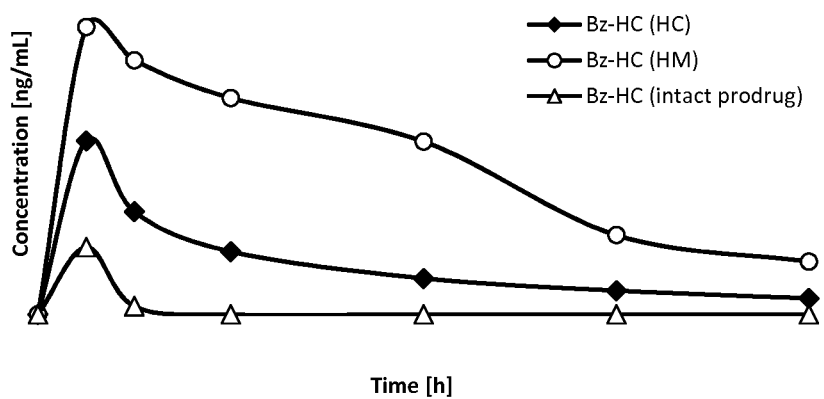
FIG. 14. PK profile graph of plasma concentrations of intact Bz-HC, active metabolite hydromorphone and of hydrocodone released from Bz-HC over time upon oral administration in rats.

Oral PK Profiles of Conjugated Hydrocodone, Hydrocodone, and Hydromorphone in Rats After oral administration of benzoate-hydrocodone (Bz-HC) to rats, PK curves were determined for intact Bz-HC, hydrocodone, and the active metabolite hydromorphone. Rats were orally administered an amount of the conjugate equivalent to 2 mg/kg of freebase hydrocodone and the plasma concentrations of intact Bz-HC, released hydrocodone, and the active metabolite, hydromorphone, were measured over time by LC-MS/MS. As shown in FIG. 14, the exposure to intact Bz-HC prodrug was much lower than the exposure to hydrocodone or hydromorphone (the AUC for intact Bz-HC was approximately 10% and 3% of the AUC values for hydrocodone and hydromorphone, respectively).

Example 9

Oral PK Profiles of Conjugated Hydrocodone, Hydrocodone, and Hydromorphone in Dogs After oral administration of benzoate-hydrocodone (Bz-HC) or Hydrocodone•BT to dogs, PK curves were determined for intact Bz-HC (Bz-HC arm only), hydrocodone, and the active metabolite hydromorphone. Dogs were orally administered an amount of Hydrocodone•BT or the conjugate equivalent to 2 mg/kg of freebase hydrocodone. The plasma concentrations of intact Bz-HC, released hydrocodone, and the active metabolite, hydromorphone, were measured over time by LC-MS/MS.

Figure 15:
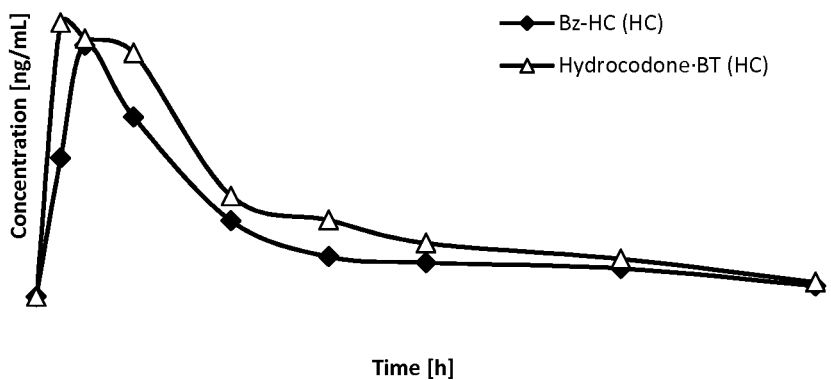
FIG. 15. PK profile graph of plasma concentrations of hydrocodone released from Bz-HC and hydrocodone•BT over time upon oral administration in dogs.

A comparison of plasma concentrations of hydrocodone released from Bz-HC and Hydrocodone•BT is shown in FIG. 15. Overall, the plasma concentrations of hydrocodone generated by both compounds were quite similar. The systemic exposure to hydrocodone was somewhat reduced for Bz-HC when compared to Hydrocodone•BT (the AUC value of hydrocodone for Bz-HC was approximately 72% of the AUC value for Hydrocodone•BT). The $C_{max}$ value of hydrocodone for Bz-HC was approximately 92% of the $C_{max}$ value for Hydrocodone•BT.

Figure 16:
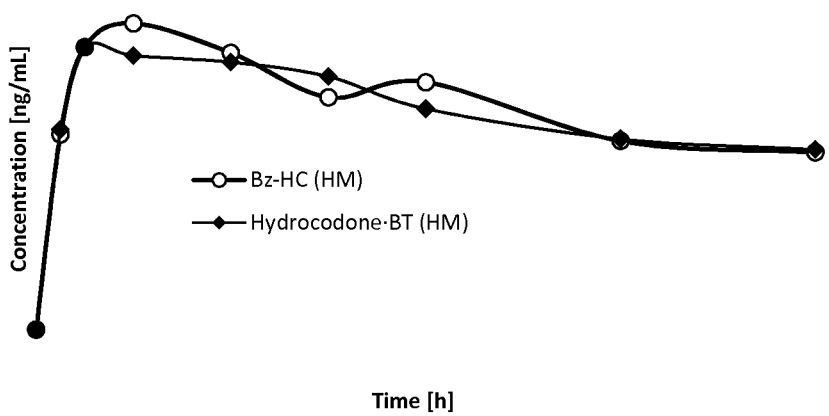
FIG. 16. PK profile graph of plasma concentrations of active metabolite hydromorphone over time upon oral administration of Bz-HC and hydrocodone•BT in dogs.
Figure 17:
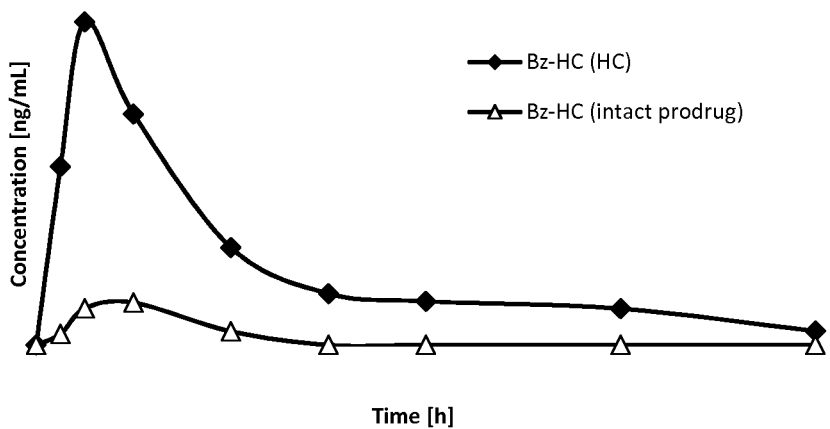
FIG. 17. PK profile graph of plasma concentrations of intact Bz-HC and of hydrocodone released from Bz-HC over time upon oral administration in dogs.

A comparison of the plasma concentrations of the active metabolite, hydromorphone, following oral administration of Bz-HC or Hydrocodone•BT is shown in FIG. 16. Systemic exposure and maximum plasma concentrations of hydromorphone were similar for both compounds. The AUC and $C_{max}$ values of hydromorphone for Bz-HC were approximately 103% and 109% of the respective values for Hydrocodone•BT A comparison the plasma concentrations of intact Bz-HC and hydrocodone released from Bz-HC is shown in FIG. 17. Similar to the results seen in rats, the plasma concentrations of intact Bz-HC prodrug in dogs were low when compared to the plasma concentrations of hydrocodone (the AUC value for intact Bz-HC was approximately 10% of the AUC value for hydrocodone).

Example 10

Figure 18:
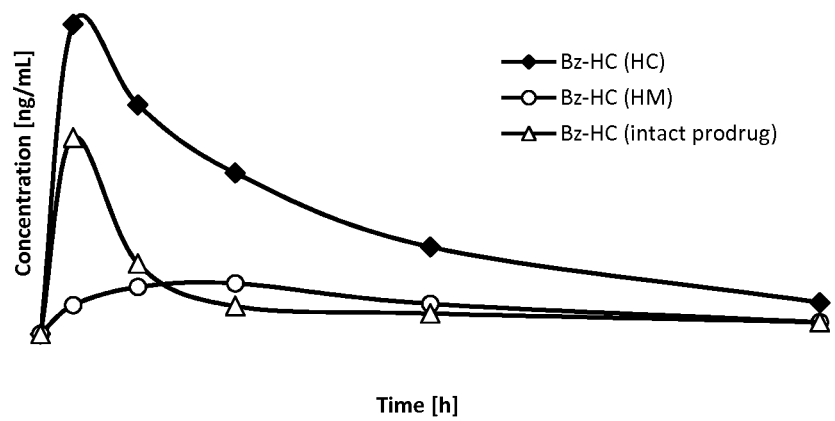
FIG. 18. PK profile graph of plasma concentrations of intact Bz-HC, active metabolite hydromorphone and of hydrocodone released from Bz-HC over time upon intravenous administration in rats at 0.30 mg/kg.

Intravenous PK Profiles of Conjugated Hydrocodone, Hydrocodone, and Hydromorphone in Rats Bz-HC (0.30 mg/kg) was administered intravenously to rats. Due to its poor water solubility (or solubility in PBS), 0.30 mg/kg was close to the maximum dose that could be administered intravenously to rats. PK curves were determined for intact Bz-HC, hydrocodone, and the active metabolite hydromorphone. The plasma concentrations of intact Bz-HC, released hydrocodone, and the active metabolite, hydromorphone, were measured over time by LC-MS/MS. The resulting PK curves are shown in FIG. 18.

Example 11

Figure 19:
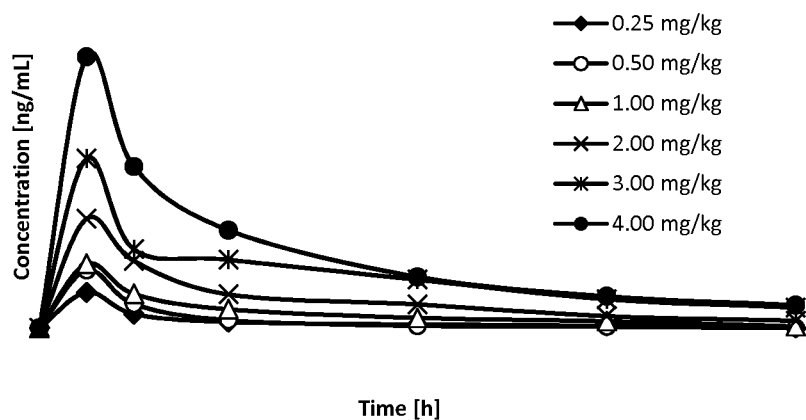
FIG. 19. PK profile graph of plasma concentrations of hydrocodone released from Bz-HC over time upon oral administration in rats at six different dosages.
Figure 20:
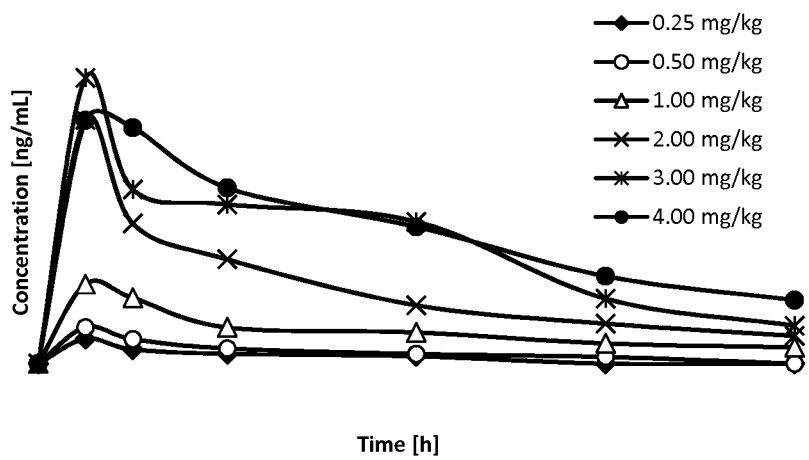
FIG. 20. PK profile graph of plasma concentrations of active metabolite hydromorphone over time upon oral administration of Bz-HC in rats at six different dosages.

Oral PK Profiles of Hydrocodone and Hydromorphone Following Various Dosages of Bz-HC in Rats Bz-HC was orally administered to rats at dosages of 0.25, 0.50, 1.00, 2.00, 3.00, or 4.00 mg/kg. The plasma concentrations of hydrocodone or hydromorphone were measured by LC-MS/MS, as demonstrated in FIGS. 19 and 20, respectively. The exposures (AUC) to hydrocodone and hydromorphone at doses of Bz-HC between 0.25 and 4.00 mg/kg were fairly linear. The respective $C_{max}$ values, however, were more variable, particularly for hydromorphone. The maximum plasma concentrations of hydromorphone did not significantly change at doses above 2.00 mg/kg of Bz-HC.

In the present specification, use of the singular includes the plural except where specifically indicated.

The compositions, prodrugs, and methods described herein can be illustrated by the following embodiments enumerated in the numbered paragraphs that follow:

1. A composition comprising at least one conjugate of hydrocodone and at least one benzoic acid or benzoic acid derivative, a salt thereof, or a combination thereof, at least one benzoic acid or benzoic acid derivative having the following formula I:

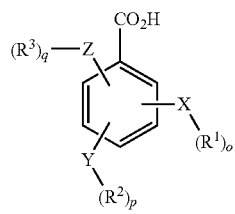

(I)

wherein,
X, Y and Z are independently selected from the group consisting of H, O, S, NH and —$(CH_2)_x$—;
$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;
o, p, q are independently selected from 0 or 1; and
x is an integer between 1 and 10.

2. A composition comprising at least one conjugate of hydrocodone and at least one benzoic acid, a derivative thereof, or a combination thereof.

3. A composition comprising a benzoate conjugate, wherein the benzoate conjugate comprises at least one hydrocodone conjugated to at least one benzoic acid or benzoic acid derivative.

4. The composition of paragraph 1, wherein at least one benzoic acid or benzoic acid derivative is an aminobenzoate, a hydroxybenzoate, an aminohydroxybenzoate, a derivative thereof, or combination thereof.

5. The composition of paragraph 4, wherein the aminobenzoate is selected from the group consisting of: anthranilic acid, 3-aminobenzoic acid, 4,5-dimethylanthranilic acid, N-methylanthranilic acid, N-acetylanthranilic acid, fenamic acids (e.g., tolfenamic acid, mefenamic acid, flufenamic acid), 2,4-diaminobenzoic acid (2,4-DABA), 2-acetylamino-4-aminobenzoic acid, 4-acetylamino-2-aminobenzoic acid, 2,4-diacetylaminobenzoic acid, derivatives thereof and combinations thereof.

6. The composition of paragraph 4, wherein the hydroxybenzoate is selected from the group consisting of salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflusinal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, 3,4,5-trimethoxybenzoic acid, derivatives thereof and combinations thereof.

7. The composition of paragraph 4, wherein the aminohydroxybenzoate is selected from the group consisting of 4-aminosalicylic acid, 3-hydroxyanthranilic acid, 3-methoxyanthranilic acid, derivatives thereof and combinations thereof.

8. The composition of paragraph 1, 2, 3, or 4, wherein at least one conjugate is a treatment or preventative composition used to treat narcotic or opioid abuse or prevent withdrawal.

9. The composition of paragraph 1, 2, 3, or 4, wherein at least one conjugate is a pain treatment composition.

10. The composition of paragraph 1, 2, 3, or 4, wherein at least one conjugate is moderate to severe pain treatment composition.

11. The composition of paragraph 1, 2, 3, or 4, wherein at least one conjugate reduces or prevents oral, intranasal or intravenous drug abuse.

12. The composition of paragraph 1, 2, 3, or 4, wherein at least one conjugate provides oral, intranasal or parenteral drug abuse resistance.

13. The composition of paragraph 1, 2, 3, or 4, wherein at least one conjugate exhibits an improved rate of release over time and AUC when compared to unconjugated hydrocodone over the same time period.

14. The composition of paragraph 1, 2, 3, or 4, wherein at least one conjugate exhibits less variability in the oral PK profile when compared to unconjugated hydrocodone.

15. The composition of paragraph 1, 2, 3, or 4, wherein at least one conjugate has reduced side effects when compared with unconjugated hydrocodone.

16. The composition of paragraph 1, 2, 3, or 4, wherein at least one conjugate prevents drug tampering by either physical or chemical manipulation.

17. The composition of paragraph 1, 2, 3, or 4, wherein at least one conjugate is provided in a dosage form selected from the group consisting of: a tablet, a capsule, a caplet, a suppository, a troche, a lozenge, an oral powder, a solution, an oral film, a thin strip, a slurry, and a suspension.

18. The composition of paragraph 1, 2, 3, or 4, wherein at least one conjugate is provided in an amount sufficient to provide a therapeutically bioequivalent AUC when compared to unconjugated hydrocodone.

19. The composition of paragraph 1, 2, 3, or 4, wherein at least one conjugate is provided in an amount sufficient to provide a therapeutically bioequivalent AUC and $C_{max}$ compared to an equivalent molar amount of unconjugated hydrocodone.

20. The composition of paragraph 1, 2, 3, or 4, wherein at least one conjugate is provided in an amount sufficient to provide a therapeutically bioequivalent AUC and a lower $C_{max}$ compared to an equivalent molar amount of unconjugated hydrocodone.
21. The composition of paragraph 1, 2, 3 or 4, wherein at least one conjugate is present in an amount of from about 0.5 mg or higher.
22. The composition of paragraph 1, 2, 3 or 4, wherein at least one conjugate is present in an amount of from about 2.5 mg or higher.
23. The composition of paragraph 1, 2, 3 or 4, wherein at least one conjugate is present in an amount of from about 5 mg or higher.
24. The composition of paragraph 1, 2, 3 or 4, wherein at least one conjugate is present in an amount of from about 10 mg or higher.
25. The composition of paragraph 1, 2, 3 or 4, wherein at least one conjugate is present in an amount of from about 20 mg or higher.
26. The composition of paragraph 1, 2, 3 or 4, wherein at least one conjugate is present in an amount of from about 50 mg or higher.
27. The composition of paragraph 1, 2, 3 or 4, wherein at least one conjugate is present in an amount of from about 100 mg or higher.
28. A method for treating a patient having a disease, disorder or condition requiring or mediated by binding of an opioid to opioid receptors of the patient, comprising orally administering to the patient a pharmaceutically effective amount of at least one conjugate of hydrocodone and at least one benzoic acid or benzoic acid derivative, a salt thereof, or a combination thereof, the benzoic acid or benzoic acid derivative having formula I:

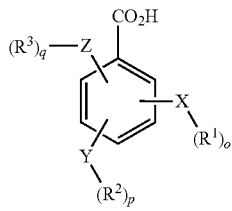

(I)

wherein
X, Y and Z are independently selected from the group consisting of H, O, S, NH and —(CH$_2$)$_x$—;
R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;
o, p, q are independently selected from 0 or 1; and
x is an integer between 1 and 10.
29. The method of paragraph 28, wherein at least one conjugate exhibits a slower rate of release over time and greater AUC when compared to an equivalent molar amount of unconjugated hydrocodone over the same time period.
30. The method of paragraph 28, wherein at least one conjugate exhibits less variability in the oral PK profile when compared to unconjugated hydrocodone.
31. The method of paragraph 28, wherein at least one conjugate has reduced side effects when compared with unconjugated hydrocodone.
32. The method of paragraph 28, wherein at least one conjugate is provided in a dosage form selected from the group consisting of: a tablet, a capsule, a caplet, a suppository, a troche, a lozenge, an oral powder, a solution, an oral film, a thin strip, a slurry, and a suspension.
33. The method of paragraph 28, wherein at least one conjugate is provided in an amount sufficient to provide a therapeutically bioequivalent AUC when compared to a molar equivalent amount of unconjugated hydrocodone.
34. The method of paragraph 28, wherein at least one conjugate is provided in an amount sufficient to provide a therapeutically bioequivalent AUC and when compared to a molar equivalent amount of unconjugated hydrocodone.
35. The method of paragraph 28, wherein at least one conjugate is provided in an amount sufficient to provide a therapeutically bioequivalent AUC and a lower $C_{max}$ when compared to a molar equivalent amount of unconjugated hydrocodone.
36. The method of paragraph 28, wherein at least one conjugate is present in an amount of from about 0.5 mg or higher.
37. The method of paragraph 28, wherein at least one conjugate is present in an amount of from about 2.5 mg or higher.
38. The method of paragraph 28, wherein at least one conjugate is present in an amount of from about 5 mg or higher.
39. The method of paragraph 28, wherein at least one conjugate is present in an amount of from about 10 mg or higher.
40. The method of paragraph 28, wherein at least one conjugate is present in an amount of from about 20 mg or higher.
41. The method of paragraph 28, wherein at least one conjugate is present in an amount of from about 50 mg or higher.
42. The method of paragraph 28, wherein at least one conjugate is present in an amount of from about 100 mg or higher.
43. The method of paragraph 28, wherein at least one conjugate binds reversibly to the opioid receptors of the patient.
44. The method of paragraph 28, wherein at least one conjugate binds reversibly to the opioid receptors of the patient without a CNS depressive effect.
45. The method of paragraph 28, wherein at least one conjugate prevents or reduces at least one constipatory side effect of unconjugated hydrocodone.
46. The method of paragraph 28, wherein at least one conjugate exhibits reduced or prevented constipatory effects when compared with unconjugated hydrocodone.
47. The method of paragraph 28, wherein at least one conjugate binds irreversibly to the opioid receptors of the patient.
48. The method of paragraph 28, wherein at least one conjugate binds irreversibly to the opioid receptors of the patient without a CNS depressive effect.
49. A method for treating a patient having a disease, disorder or condition requiring or mediated by inhibiting binding of an opioid to opioid receptors of the patient, comprising orally administering to the patient a pharmaceutically effective amount of at least one conjugate of hydrocodone and at least one benzoic acid or benzoic acid derivative, a salt thereof, or a combination thereof, the benzoic acid or benzoic acid derivative having formula I:

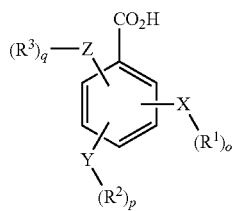

(I)

wherein

X, Y and Z are independently selected from the group consisting of H, O, S, NH and $-(CH_2)_x-$;

$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;

o, p, q are independently selected from 0 or 1; and x is an integer between 1 and 10.

50. The method of paragraph 49, wherein at least one conjugate reversibly inhibits binding of an opioid to the opioid receptor of the patient.

51. The method of paragraph 49, wherein at least one conjugate reversibly inhibits binding of an opioid to the opioid receptor of the patient without a CNS depressive effect.

52. The method of paragraph 49, wherein at least one conjugate prevents or reduces at least one constipatory side effect of hydrocodone alone.

53. A method for treating a patient having a disease, disorder or condition requiring or mediated by binding of an opioid to opioid receptors of the patient, comprising orally administering to the patient a pharmaceutically effective amount of at least one conjugate of hydrocodone and at least one benzoic acid, a salt thereof, a derivative thereof or a combination thereof.

54. The method of paragraph 53, wherein at least one conjugate provides a slower rate of release over time and higher AUC when compared to an equivalent molar amount of unconjugated hydrocodone over the same time period.

55. The method of paragraph 53, wherein at least one conjugate exhibits less variability in the oral PK profile when compared to hydrocodone alone.

56. The method of paragraph 53, wherein at least one conjugate has reduced side effects when compared with hydrocodone alone.

57. The method of paragraph 53, wherein at least one conjugate is provided in a dosage form selected from the group consisting of: a tablet, a capsule, a caplet, a suppository, a troche, a lozenge, an oral powder, a solution, an oral film, a thin strip, a slurry, and a suspension.

58. The method of paragraph 53, wherein at least one conjugate is provided in an amount sufficient to provide a therapeutically bioequivalent AUC when compared to hydrocodone alone.

59. The method of paragraph 53, wherein at least one conjugate is provided in an amount sufficient to provide a therapeutically bioequivalent AUC and $C_{max}$ when compared to hydrocodone alone.

60. The method of paragraph 53, wherein at least one conjugate is provided in an amount sufficient to provide a therapeutically bioequivalent AUC when compared to hydrocodone alone with a lower $C_{max}$.

61. The method of paragraph 53, wherein at least one conjugate is provided in an amount sufficient to provide a therapeutically bioequivalent AUC when compared to hydrocodone alone, but does not provide an equivalent $C_{max}$.

62. The method of paragraph 53, wherein at least one conjugate is present in an amount of from about 0.5 mg or higher.

63. The method of paragraph 53, wherein at least one conjugate is present in an amount of from about 2.5 mg or higher.

64. The method of paragraph 53, wherein at least one conjugate is present in an amount of from about 5 mg or higher.

65. The method of paragraph 53, wherein at least one conjugate is present in an amount of from about 10 mg or higher.

66. The method of paragraph 53, wherein at least one conjugate is present in an amount of from about 20 mg or higher.

67. The method of paragraph 53, wherein at least one conjugate is present in an amount of from about 50 mg or higher.

68. The method of paragraph 53, wherein at least one conjugate is present in an amount of from about 100 mg or higher.

69. The method of paragraph 53, wherein at least one conjugate binds reversibly to the opioid receptors of the patient.

70. The method of paragraph 53, wherein at least one conjugate binds reversibly to the opioid receptors of the patient without a CNS depressive effect.

71. The method of paragraph 53, wherein at least one conjugate prevents or reduces at least one constipatory side effect of hydrocodone alone.

72. The method of paragraph 53, wherein at least one conjugate exhibits reduced or prevented constipatory effects.

73. The method of paragraph 53, wherein at least one conjugate binds permanently to the opioid receptors of the patient.

74. The method of paragraph 53, wherein at least one conjugate binds permanently to the opioid receptors of the patient without a CNS depressive effect.

75. A method for treating a patient having a disease, disorder or condition requiring or mediated by inhibiting binding of an opioid to opioid receptors of the patient, comprising orally administering to the patient a pharmaceutically effective amount of at least one conjugate of hydrocodone and at least one benzoic acid, a salt thereof, a derivative thereof or a combination thereof.

76. The method of paragraph 75, wherein at least one conjugate reversibly inhibits binding of an opioid to the opioid receptor of the patient.

77. The method of paragraph 75, wherein at least one conjugate reversibly inhibits binding of an opioid to the opioid receptor of the patient without a CNS depressive effect.

78. The method of paragraph 75, wherein at least one conjugate prevents or reduces at least one constipatory side effect of hydrocodone alone.

79. A pharmaceutical kit comprising:

a specified amount of individual doses in a package containing a pharmaceutically effective amount of at least one conjugate of hydrocodone and at least one benzoic acid or benzoic acid derivative, a salt thereof, or a combination thereof, the benzoic acid or benzoic acid derivative having the formula I:

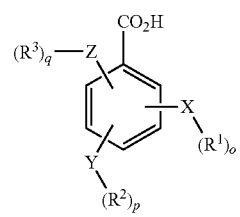

(I)

wherein

X, Y and Z are independently selected from the group consisting of H, O, S, NH and $-(CH_2)_x-$;

$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;

o, p, q can be independently selected from 0 or 1; and x is an integer between 1 and 10

80. The kit of paragraph 79, wherein the kit further comprises: (ii) instructions for use of the kit in a method for treating or preventing drug withdrawal symptoms or pain in a human or animal patient.

81. The kit of paragraph 80, wherein the patient is a pediatric patient.
82. The kit of paragraph 80, wherein the patient is an elderly patient.
83. The kit of paragraph 80, wherein the patient is a normative patient.
84. A pharmaceutical kit comprising:
a specified amount of individual doses in a package containing a pharmaceutically effective amount of at least one conjugate of hydrocodone and at least one benzoic acid, a salt thereof, a derivative thereof or a combination thereof.
85. The kit of paragraph 84, wherein the kit further comprises:
(ii) instructions for use of the kit in a method for treating or preventing drug withdrawal symptoms or pain in a human or animal patient.
86. The kit of paragraph 85, wherein the patient is a pediatric patient.
87. The kit of paragraph 85, wherein the patient is an elderly patient.
88. The kit of paragraph 85, wherein the patient is a normative patient.
89. The kit of paragraph 79, 80, 84 or 85, wherein the individual dosages comprise at least about 0.5 mg or higher of at least one conjugate.
90. The kit of paragraph 79, 80, 84 or 85, wherein the individual dosages comprise at least about 2.5 mg or higher of at least one conjugate.
91. The kit of paragraph 79, 80, 84 or 85, wherein the individual dosages comprise at least about 5.0 mg or higher of at least one conjugate.
92. The kit of paragraph 79, 80, 84 or 85, wherein the individual dosages comprise at least about 10 mg or higher of at least one conjugate.
93. The kit of paragraph 79, 80, 84 or 85, wherein the individual dosages comprise at least about 20 mg or higher of at least one conjugate.
94. The kit of paragraph 79, 80, 84 or 85, wherein the individual dosages comprise at least about 50 mg or higher of at least one conjugate.
95. The kit of paragraph 79, 80, 84 or 85, wherein the individual dosages comprise at least about 100 mg or higher of at least one conjugate.
96. The kit of paragraph 79, 80, 84 or 85, wherein the kit comprises from about 1 to about 60 individual doses.
97. The kit of paragraph 79, 80, 84 or 85, wherein the kit comprises from about 10 to about 30 individual doses.
98. A composition comprising at least one conjugate of hydrocodone and at least one heteroaryl carboxylic acid, a derivative thereof, or a combination thereof.
99. The composition of paragraph 98, wherein at least one heteroaryl carboxylic acid is selected from formula II, formula III or formula IV,
wherein formula II, formula III and formula IV are:

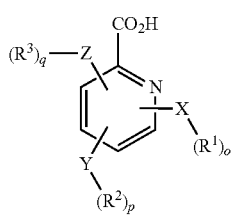

(II)

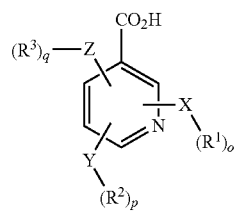

(III)

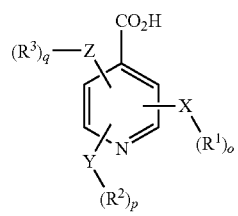

(IV)

wherein
X, Y and Z are independently selected from the group consisting of H, O, S, NH and —(CH$_2$)$_x$—;
R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;
o, p, q are independently selected from 0 or 1; and
x is an integer from 1 to 10.
100. A composition comprising at least one conjugate of hydrocodone and at least one nicotinic acid, a derivative thereof, or a combination thereof.
101. The composition of paragraph 98, wherein at least one heteroaryl carboxylic acid is a pyridine derivative.
102 The composition of paragraph 98, wherein the heteroaryl carboxylic acid is selected from the group consisting of, isonicotinic acid, picolinic acid, 3-hydroxypicolinic acid, 6-hydroxynicotinic acid, citrazinic acid, 2,6-dihydroxynicotinic acid, kynurenic acid, xanthurenic acid, 6-hydroxykynurenic acid, 8-methoxykynurenic acid, 7,8-dihydroxykynurenic acid, 7,8-dihydro-7,8-dihydroxykynurenic acid, derivatives thereof and combinations thereof.
103. The composition of paragraph 98, 99 or 100, wherein at least one conjugate is used to treat drug, narcotic or opioid abuse or prevent withdrawal.
104. The composition of paragraph 98, 99 or 100, wherein at least one conjugate is used to treat pain.
105. The composition of paragraph 98, 99 or 100, wherein at least one conjugate is used to treat moderate to severe pain.
106. The composition of paragraph 98, 99 or 100, wherein at least one conjugate reduces or prevents oral, intranasal or intravenous drug abuse.
107. The composition of paragraph 98, 99 or 100, wherein at least one conjugate provides oral, intranasal or parenteral drug abuse resistance.
108. The composition of paragraph 98, 99 or 100, wherein at least one conjugate prevents drug tampering by either physical or chemical manipulation.
109. The composition of paragraph 98, 99 or 100, wherein at least one conjugate exhibits an improved rate of release over time and AUC when compared to a molar equivalent of unconjugated hydrocodone alone over the same time period.
110. The composition of paragraph 98, 99 or 100, wherein at least one conjugate exhibits less variability in the oral PK profile when compared to a molar equivalent of unconjugated hydrocodone alone.

111. The composition of paragraph 98, 99 or 100, wherein at least one conjugate has reduced side effects when compared with hydrocodone alone.

112. The composition of paragraph 98, 99 or 100, wherein the composition is provided in a dosage form selected from the group consisting of: a tablet, a capsule, a caplet, a suppository, a troche, a lozenge, an oral powder, a solution, an oral film, a thin strip, a slurry, and a suspension.

113. The composition of paragraph 98, 99 or 100, wherein at least one conjugate is provided in an amount sufficient to provide a therapeutically bioequivalent AUC when compared to a molar equivalent of unconjugated hydrocodone alone.

114. The composition of paragraph 98, 99 or 100, wherein at least one conjugate is provided in an amount sufficient to provide a therapeutically bioequivalent AUC and $C_{max}$ when compared to hydrocodone alone.

115. The composition of paragraph 98, 99 or 100, wherein at least one conjugate is provided in an amount sufficient to provide a therapeutically bioequivalent AUC when compared to hydrocodone alone, with a lower $C_{max}$.

116. The composition of paragraph 98, 99 or 100, wherein at least one conjugate is present in an amount of from about 0.5 mg or higher.

117. The composition of paragraph 98, 99 or 100, wherein at least one conjugate is present in an amount of from about 2.5 mg or higher.

118. The composition of paragraph 98, 99 or 100, wherein at least one conjugate is present in an amount of from about 5 mg or higher.

119. The composition of paragraph 98, 99 or 100, wherein at least one conjugate is present in an amount of from about 10 mg or higher.

120. The composition of paragraph 98, 99 or 100, wherein at least one conjugate is present in an amount of from about 20 mg or higher.

121. The composition of paragraph 98, 99 or 100, wherein at least one conjugate is present in an amount of from about 50 mg or higher.

122. The composition of paragraph 98, 99 or 100, wherein at least one conjugate is present in an amount of from about 100 mg or higher.

123. A method for treating a patient having a disease, disorder or condition requiring or mediated by binding of an opioid to opioid receptors of the patient, comprising orally administering to the patient a pharmaceutically effective amount of at least one conjugate of hydrocodone and at least one heteroaryl carboxylic acid.

124. The method of paragraph 123, wherein at least one heteroaryl carboxylic acid is selected from formula II, formula III or formula IV, wherein formula II, formula III and formula IV are:

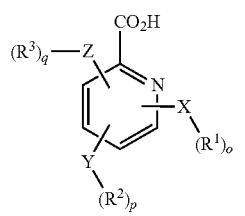

(II)

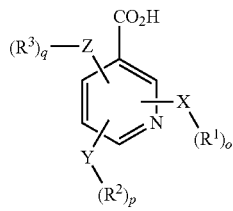

(III)

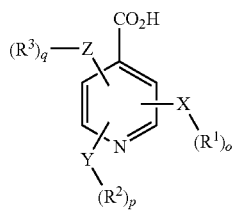

(IV)

wherein
X, Y and Z are independently selected from the group consisting of H, O, S, NH and —(CH$_2$)$_x$—;
R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;
o, p, q are independently selected from 0 or 1; and
x is an integer from 1 to 10.

125. A method for treating a patient having a disease, disorder or condition requiring or mediated by binding of an opioid to opioid receptors of the patient, comprising orally administering to the patient a pharmaceutically effective amount of at least one conjugate of hydrocodone and at least one nicotinic acid, a derivative thereof, or a combination thereof.

126. The method of paragraph 123, 124, or 125, wherein at least one conjugate exhibits an improved rate of release over time and AUC when compared to hydrocodone alone over the same time period.

127. The method of paragraph 123, 124, or 125, wherein at least one conjugate exhibits less variability in the oral PK profile when compared to hydrocodone alone.

128. The method of paragraph 123, 124, or 125, wherein at least one conjugate has reduced side effects when compared to hydrocodone alone.

129. The method of paragraph 123, 124, or 125, wherein at least one conjugate is provided in a dosage from selected from the group consisting of: a tablet, a capsule, a caplet, a suppository, a troche, a lozenge, an oral powder, a solution, an oral film, a thin strip, a slurry, and a suspension.

130. The method of paragraph 123, 124, or 125, wherein at least one conjugate is provided in an amount sufficient to provide a therapeutically bioequivalent AUC when compared to an equivalent molar amount of unconjugated hydrocodone.

131. The method of paragraph 123, 124, or 125, wherein at least one conjugate is provided in an amount sufficient to provide a therapeutically bioequivalent AUC and $C_{max}$ when compared to an equivalent molar amount of unconjugated hydrocodone.

132. The method of paragraph 123, 124, or 125, wherein at least one conjugate is provided in an amount sufficient to provide a therapeutically bioequivalent AUC and a lower $C_{max}$ compared to the same molar amount of unconjugated hydrocodone.

133. The method of paragraph 123, 124, or 125, wherein at least one conjugate is provided in an amount sufficient to provide a therapeutically bioequivalent AUC when compared to hydrocodone alone, but does not provide an equivalent $C_{max}$.

134. The method of paragraph 123, 124, or 125, wherein at least one conjugate is present in an amount of from about 0.5 mg or higher.

135. The method of paragraph 123, 124, or 125, wherein at least one conjugate is present in an amount of from about 2.5 mg or higher.

136. The method of paragraph 123, 124, or 125, wherein at least one conjugate is present in an amount of from about 5 mg or higher.

137. The method of paragraph 123, 124, or 125, wherein at least one conjugate is present in an amount of from about 10 mg or higher.

138. The method of paragraph 123, 124, or 125, wherein at least one conjugate is present in an amount of from about 20 mg or higher.

139. The method of paragraph 123, 124, or 125, wherein at least one conjugate is present in an amount of from about 50 mg or higher.

140. The method of paragraph 123, 124, or 125, wherein at least one conjugate is present in an amount of from about 100 mg or higher.

141. The method of paragraph 123, 124, or 125, wherein at least one conjugate binds reversibly to the opioid receptors of the patient.

142. The method of paragraph 123, 124, or 125, wherein at least one conjugate binds reversibly to the opioid receptors of the patient without a CNS depressive effect.

143. The method of paragraph 123, 124, or 125, wherein at least one conjugate prevents or reduces at least one constipatory side effect of hydrocodone alone.

144. The method of paragraph 123, 124, or 125, wherein at least one conjugate exhibits reduced or prevented constipatory effects.

145. The method of paragraph 123, 124, or 125, wherein at least one conjugate binds permanently to the opioid receptors of the patient.

146. The method of paragraph 123, 124, or 125, wherein at least one conjugate binds permanently to the opioid receptors of the patient without a CNS depressive effect.

147. A method for treating a patient having a disease, disorder or condition requiring or mediated by inhibiting binding of an opioid to opioid receptors of the patient, comprising orally administering to the patient a pharmaceutically effective amount of at least one conjugate of hydrocodone and at least one heteroaryl carboxylic acid.

148. The method of paragraph 147, wherein at least one heteroaryl carboxylic acid is selected from formula II, formula III or formula IV, wherein formula II, formula III and formula IV are:

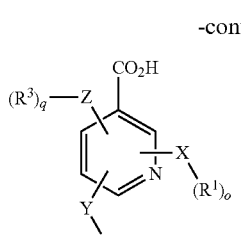

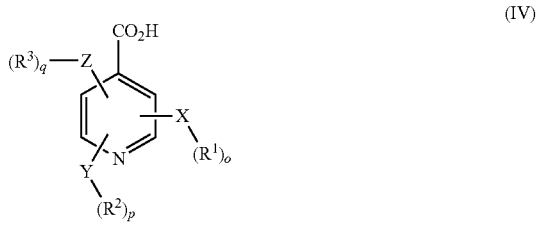

wherein
X, Y and Z are independently selected from the group consisting of H, O, S, NH and $-(CH_2)_x-$;
$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;
o, p, q are independently selected from 0 or 1; and
x is an integer from 1 to 10.

149. A method for treating a patient having a disease, disorder or condition requiring or mediated by inhibiting binding of an opioid to opioid receptors of the patient, comprising orally administering to the patient a pharmaceutically effective amount of at least one conjugate of hydrocodone and at least one nicotinic acid, a derivative thereof, or a combination thereof.

150. The method of paragraph 147, 148, or 149, wherein at least one conjugate reversibly inhibits binding of an opioid to the opioid receptor of the patient.

151. The method of paragraph 147, 148, or 149, wherein at least one conjugate reversibly inhibits binding of an opioid to the opioid receptor of the patient without a CNS depressive effect.

152. The method of paragraph 147, 148, or 149, wherein at least one conjugate prevents or reduces at least one constipatory side effect of hydrocodone alone.

153. A pharmaceutical kit comprising:
a specified number of individual doses in a package containing a pharmaceutically effective amount of at least one conjugate of hydrocodone and at least one heteroaryl carboxylic acid, a derivative thereof, or a combination thereof, wherein at least one heteroaryl carboxylic acid is selected from formula II, formula III or formula IV, wherein formula II, formula III and formula IV are:

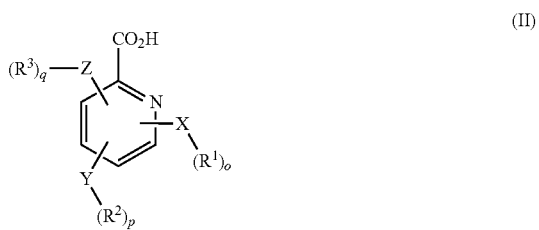

-continued

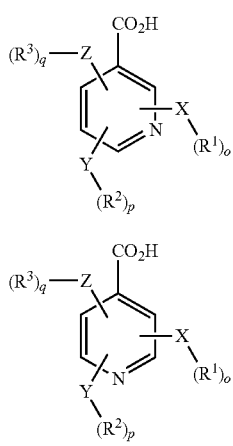

wherein
X, Y and Z are independently selected from the group consisting of H, O, S, NH and —$(CH_2)_x$—;
$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;
o, p, q are independently selected from 0 or 1; and
x is an integer from 1 to 10.

154. The kit of paragraph 153, wherein the kit further comprises:
(ii) instructions for use of the kit in a method for treating or preventing drug withdrawal symptoms or pain in a human or animal patient.

155. The kit of paragraph 154, wherein the patient is a pediatric patient.

156. The kit of paragraph 154, wherein the patient is an elderly patient.

157. The kit of paragraph 154, wherein the patient is a normative patient.

158. The kit of paragraph 153 or 154, wherein the individual dosages comprise at least about 0.5 mg or higher of at least one conjugate.

159. The kit of paragraph 153 or 154, wherein the individual dosages comprise at least about 2.5 mg or higher of at least one conjugate.

160. The kit of paragraph 153 or 154, wherein the individual dosages comprise at least about 5.0 mg or higher of at least one conjugate.

161. The kit of paragraph 153 or 154, wherein the individual dosages comprise at least about 10 mg or higher of at least one conjugate.

162. The kit of paragraph 153 or 154, wherein the individual dosages comprise at least about 20 mg or higher of at least one conjugate.

163. The kit of paragraph 153 or 154, wherein the individual dosages comprise at least about 50 mg or higher of at least one conjugate.

164. The kit of paragraph 153 or 154, wherein the individual dosages comprise at least about 100 mg or higher of at least one conjugate.

165. The kit of paragraph 153 or 154, wherein the kit comprises from about 1 to about 60 individual doses.

166. The kit of paragraph 153 or 154, wherein the kit comprises from about 10 to about 30 individual doses.

167. A prodrug comprising at least one conjugate of hydrocodone and at least one benzoic acid or benzoic acid derivative, a salt thereof, a or a combination thereof, the benzoic acid or benzoic acid derivative having the following formula I:

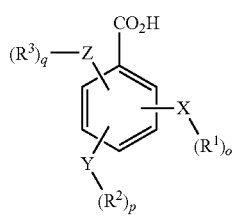

wherein,
X, Y and Z are independently selected from the group consisting of H, O, S, NH and —$(CH_2)_x$—;
$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;
o, p, q are independently selected from 0 or 1; and
x is an integer between 1 and 10.

168. A prodrug comprising at least one conjugate of hydrocodone and at least one benzoic acid, a derivative thereof, or a combination thereof.

169. A prodrug comprising a benzoate conjugate, wherein the benzoate conjugate comprises at least one hydrocodone conjugated to at least one benzoic acid or benzoic acid derivative.

170. A prodrug comprising at least one conjugate of hydrocodone and at least one heteroaryl carboxylic acid, a derivative thereof, or a combination thereof.

171. The prodrug of paragraph 170, wherein the heteroaryl carboxylic acid is selected from formula II, formula III or formula IV,
wherein formula II, formula III and formula IV are:

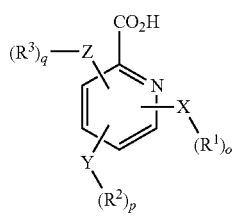

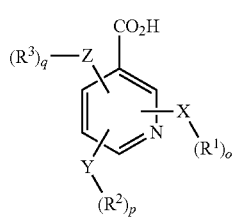

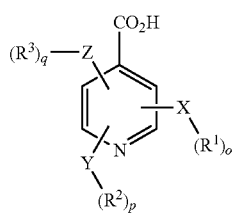

wherein
X, Y and Z are independently selected from the group consisting of H, O, S, NH and —(CH$_2$)$_x$—;
R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;
o, p, q are independently selected from 0 or 1; and
x is an integer from 1 to 10.

172. A prodrug comprising at least one conjugate of hydrocodone and at least one nicotinic acid, a derivative thereof, or a combination thereof.

173. The prodrug of paragraph 167, wherein the benzoic acid derivative is an aminobenzoate, a hydroxybenzoate, an aminohydroxybenzoate, a derivative thereof, or combination thereof.

174. The composition of paragraph 1 or 2, wherein at least one conjugate exhibits less variability in intranasal PK profiles when compared to unconjugated hydrocodone.

175. The composition of paragraph 1 or 2, wherein at least one conjugate exhibits less variability in the parenteral PK profiles when compared to unconjugated hydrocodone.

176. The composition of paragraph 1 or 2, wherein at least one conjugate exhibits less variability in the intravenous PK profile when compared to unconjugated hydrocodone.

The presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

The invention claimed is:

1. A composition comprising acetaminophen and a conjugate, wherein the conjugate is benzoate-hydrocodone (Bz-HC) having the following structure:

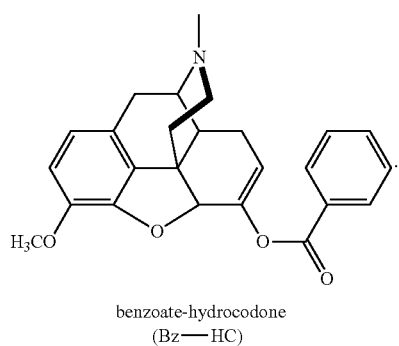

benzoate-hydrocodone
(Bz—HC)

2. The composition of claim 1, wherein the conjugate is used to treat narcotic or opioid abuse; to reduce narcotic or opioid withdrawal; to treat moderate to severe pain; to reduce oral, intranasal or intravenous drug abuse; or to provide oral, intranasal or parenteral drug abuse resistance.

3. The composition of claim 1, wherein the conjugate exhibits an improved AUC and rate of release over time when compared to unconjugated hydrocodone over the same time period; exhibits less variability in the oral PK profile when compared to unconjugated hydrocodone; or has reduced side effects when compared with unconjugated hydrocodone.

4. The composition of claim 1, wherein the conjugate is provided in a dosage form selected from the group consisting of: a tablet, a capsule, a caplet, a suppository, a troche, a lozenge, an oral powder, a solution, an oral film, a thin strip, a slurry, and a suspension.

5. The composition of claim 1, wherein the conjugate is provided in an amount sufficient to provide a therapeutically bioequivalent AUC when compared to unconjugated hydrocodone.

6. The composition of claim 1, wherein the conjugate is provided in an amount sufficient to provide a therapeutically bioequivalent AUC and $C_{max}$ when compared to an equivalent molar amount of unconjugated hydrocodone.

7. The composition of claim 1, wherein the conjugate is provided in an amount sufficient to provide a therapeutically bioequivalent AUC and a lower $C_{max}$ when compared to an equivalent molar amount of unconjugated hydrocodone.

8. The composition of claim 1, wherein the conjugate is a salt.

9. The composition of claim 8, wherein the salt is a hydrochloride/chloride.

10. The composition of claim 1, further comprising a biologically acceptable carrier.

11. The composition of claim 1, wherein upon administration, active hydrocodone is released from the conjugate through first-pass metabolism.

12. A method for treating pain in an individual in need thereof comprising the step of orally administering a pharmaceutically effective amount of a composition comprising acetaminophen and a conjugate, wherein the conjugate is benzoate-hydrocodone (Bz-HC) having the following structure:

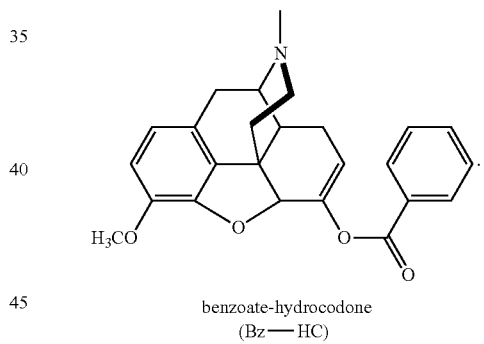

benzoate-hydrocodone
(Bz—HC)

13. The method of claim 12, wherein the conjugate exhibits an improved AUC and rate of release over time when compared to unconjugated hydrocodone over the same time period; exhibits less variability in the oral PK profile when compared to unconjugated hydrocodone; or has reduced side effects when compared with unconjugated hydrocodone.

14. The method of claim 12, wherein the composition is provided in a dosage form selected from the group consisting of: a tablet, a capsule, a caplet, a suppository, a troche, a lozenge, an oral powder, a solution, an oral film, a strip, a slurry, and a suspension.

15. The method of claim 12, wherein the conjugate is provided in an amount sufficient to provide a therapeutically bioequivalent AUC when compared to unconjugated hydrocodone.

16. The method of claim 12, wherein the conjugate is provided in an amount sufficient to provide a therapeutically bioequivalent AUC and $C_{max}$ when compared to an equivalent molar amount of unconjugated hydrocodone.

17. The method of claim 12, wherein the conjugate is provided in an amount sufficient to provide a therapeutically bioequivalent AUC and a lower $C_{max}$ when compared to an equivalent molar amount of unconjugated hydrocodone.

18. The method of claim 12, wherein the composition is used for treating pain mediated by binding of an opioid primarily to µ opioid receptors of the patient.

19. The method of claim 18, wherein the conjugate binds reversibly to the µ opioid receptors of the patient.

20. The method of claim 18, wherein the conjugate binds reversibly to the µ opioid receptors of the patient without a CNS depressive effect.

21. The method of claim 12, wherein the composition also reduces narcotic or opioid abuse.

22. The method of claim 12, wherein the composition also reduces narcotic or opioid withdrawal.

23. The method of claim 12, wherein the composition also reduces oral, intranasal or intravenous narcotic or opioid abuse.

24. The method of claim 12, wherein the composition also provides oral, intranasal or parenteral non corticoid opioid abuse resistance.

25. A pharmaceutical kit comprising a specified amount of individual doses in a package containing a pharmaceutically effective amount of acetaminophen and a conjugate, wherein the conjugate is benzoate-hydrocodone (Bz-HC) having the following structure:

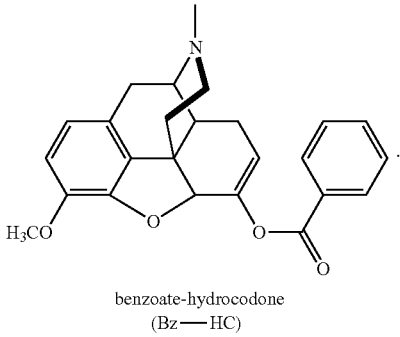

benzoate-hydrocodone
(Bz—HC)

26. The pharmaceutical kit of claim 25, wherein the kit further comprises instructions for use of the kit in a method for treating pain.

27. The pharmaceutical kit of claim 25, wherein the kit further comprises instructions for use of the kit in a method for treating narcotic or opioid withdrawal symptoms.

28. The pharmaceutical kit of claim 25, wherein the kit further comprises instructions for use of the kit in a method for reducing narcotic or opioid abuse.

29. The pharmaceutical kit of claim 25, wherein the specified amount of individual doses comprise from about 1 to about 100 individual dosages.

30. The pharmaceutical kit of claim 25, wherein the individual doses comprise at least about 0.5 mg of the conjugate.

* * * * *